United States Patent
Andrés-Gil et al.

(10) Patent No.: US 8,329,704 B2
(45) Date of Patent: Dec. 11, 2012

(54) SUBSTITUTED PYRAZINONE DERIVATIVES FOR USE IN MCH-1 MEDIATED DISEASES

(75) Inventors: José Ignacio Andrés-Gil, Madrid (ES); Manuel Jesús Alcázar-Vaca, Toledo (ES); Rosa María Álvarez-Escobar, Toledo (ES); Julen Oyarzabal Santamarina, Olias del Rey (Toledo) (ES); Frank Matthias Dautzenberg, Vosselaar (BE); Jacqueline Macritchie, Saffron Walden (GB); Donald Simpson, Haverhill (GB); Sonia Martinez Gonzalez, Tres Cantos (Madrid) (ES)

(73) Assignee: Janssen Pharmaceutica, N.V., Beerse (BE)

( * ) Notice: Subject to any disclaimer, the term of this patent is extended or adjusted under 35 U.S.C. 154(b) by 870 days.

(21) Appl. No.: 12/091,365

(22) PCT Filed: Dec. 18, 2006

(86) PCT No.: PCT/EP2006/069830
§ 371 (c)(1),
(2), (4) Date: Apr. 24, 2008

(87) PCT Pub. No.: WO2007/071646
PCT Pub. Date: Jun. 28, 2007

(65) Prior Publication Data
US 2009/0012062 A1     Jan. 8, 2009

(30) Foreign Application Priority Data
Dec. 21, 2005   (EP) .................................... 05112616

(51) Int. Cl.
*A61K 31/4965* (2006.01)
*C07D 241/02* (2006.01)
(52) U.S. Cl. .................................... 514/255.05; 544/408
(58) Field of Classification Search ........................ None
See application file for complete search history.

(56) References Cited

FOREIGN PATENT DOCUMENTS

| WO | WO 98/11075 A1 | 3/1998 |
|---|---|---|
| WO | WO 03/033476 A1 | 4/2003 |
| WO | WO 03/033480 A1 | 4/2003 |
| WO | WO 03/097047 A1 | 11/2003 |
| WO | WO 2004/011438 A1 | 2/2004 |
| WO | WO 2004/024702 A1 | 3/2004 |
| WO | WO 2005/040157 A2 | 5/2005 |
| WO | WO 2005/042541 A1 | 5/2005 |
| WO | WO 2005/070898 A1 | 8/2005 |
| WO | WO 2005/070925 A1 | 8/2005 |
| WO | WO 2005/085200 A1 | 9/2005 |
| WO | WO 2005/103039 A1 | 11/2005 |

OTHER PUBLICATIONS

Buysens, et. al., Tetrahedron (1995), 51(45), 12463-78.*

Berry, M.D. et al., "Aliphatic Propargylamines Rescue From Permanent Focal Ischemia When Administered 5 Hours Following Insult", Society for Neuroscience, 2001, pp. 2024, vol. 27, Abstract 763.9.
Bittencourt, J.C. et al., "The Melanin-Concentrating Hormone System of the Rat Brain: An Immuno- and Hybridization Histochemical Characterization", The Journal of Comparative Neurology, (1992) pp. 218-245, vol. 319.
Borowsky, Beth et al., "Antidepressant, anxiolytic and anorectic effects of a melanin-concentrating hormone-1 receptor antagonist", Nature Medicine, Aug. 2002, pp. 825-830, vol. 8, No. 8.
Chaki, Shigeyuki et al., "MGS0039: a potent and selective group II metabotropic glutamate receptor antagonist with antidepressant-like activity", Neuropharmacology, (2004), pp. 457-467, vol. 46.
Dyke, Hazel J. et al., "Recent developments in the discovery of MCH-1R antagonists for the treatment of obesity—an update", Review, Oct. 2005, pp. 1303-1313, vol. 15, No. 10.
Hervieu, G.J. et al., "The distribution of themRNA and protein products of the melanin-concentrating hormone (MCH) receptor gene, slc-1, in the central nervous ystem of the rat", European Journal of Neuroscience, 2000, pp. 1194-1216, vol. 12.
Kennedy, A.R. et al., "Effect of Direct Injection of Melanin-Concentrating Hormone into the Paraventricular Nucleus: Further Evidence for a Stimulatory Role in the Adrenal Axis via SLC-1", Journal of Neuroendocrinology, 2003, pp. 268-272 vol. 15.
Qu, Daqing et al., "A role for melanin-concentrating hormone in the central regulation of feeding behaviour", Nature, Mar. 21, 1996, pp. 243-247, vol. 380.
Saito, Yumiko et al., "Expression of the Melanin-Concentrating Hormone (MCH) Receptor mRNA in the Rat Brain", The Journal of Comparative Neurology, (2001), pp. 26-40, vol. 435.

(Continued)

*Primary Examiner* — Jeffrey Murray
(74) *Attorney, Agent, or Firm* — Peter Herridge

(57) ABSTRACT

The present invention concerns aryl and heteroaryl substituted pyrazinone derivatives having antagonistic melanin-concentrating hormone (MCH) activity, in particular MCH-1 activity according to the general Formula (I)

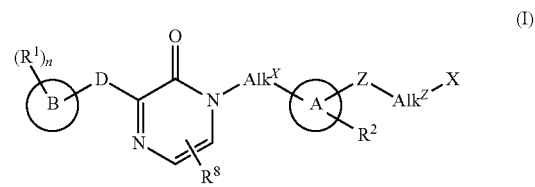

(I)

a pharmaceutically acceptable acid or base addition salt thereof, a stereochemically isomeric form thereof, an N-oxide form thereof or a quaternary ammonium salt thereof, wherein the variables are defined in Claim 1. It further relates to their preparation, compositions comprising them and their use as a medicine. The compounds according to the invention are useful for the prevention and/or treatment of psychiatric disorders, including but not limited to anxiety, eating disorders, mood disorders, such as bipolar disorders and depression, psychoses, such as schizophrenia, and sleeping disorders; obesity; diabetes; sexual disorders and neurological disorders.

13 Claims, No Drawings

OTHER PUBLICATIONS

Stella, V.J. et al., "Prodrugs Do They Have Advantages in Clinical Practice?", Drugs, (1985), pp. 455-473, vol. 29.

Stella, V.J. et al., "4. Prodrugs: the control of drug delivery via bioreversible chemical modification", Prodrugs, 1985, pp. 112-176.

Sullivan, Elaine et al., "Measurement of [$Ca^{2+}$] Using the Fluorometric Imaging Plate Reader (FLIPR)", Methods in Molecular Biology, 1999, pp. 125-133, vol. 114.

Tan, Carina P. et al., "Melanin-Concentrating Hormone Receptor Subtypes 1 and 2: Species-Specific Gene Expression", Genomics, Jun. 2002, pp. 785-792, vol. 79, No. 6.

Verret, Laure et al., "A role of melanin-concentrating hormone producing neurons in the central regulation of paradoxical sleep", BMC Neuroscience, 2003, pp. 1-10, 4:19.

* cited by examiner

SUBSTITUTED PYRAZINONE DERIVATIVES FOR USE IN MCH-1 MEDIATED DISEASES

CROSS REFERENCE TO RELATED APPLICATIONS

This application claims priority of the benefits of the filing of patent application Nos. PCT/EP2006/069830 (WO2007/071646) filed Dec. 18, 2006, and EPO Patent Application No. 05112616.7 filed Dec. 21, 2005. The complete disclosures of the aforementioned related applications are hereby incorporated herein by reference for all purposes.

FIELD OF THE INVENTION

The present invention concerns aryl and heteroaryl substituted pyrazinone derivatives having antagonistic melanin-concentrating hormone (MCH) activity, in particular MCH-1 activity. It further relates to their preparation, compositions comprising them and their use as a medicine.

BACKGROUND OF THE INVENTION

Melanin concentrating hormone (MCH) is a cyclic 19-amino acid polypeptide, which is mainly produced by hypothalamic neurons projecting widely throughout the central nervous system (CNS) (J. Comp. Neurol. (1992) 319, 218-245). MCH mediates its effects through two G protein-coupled receptors (GPCRs) termed MCH-1 and MCH-2 (reviewed in Doggrell, 2003). While in rodents only the MCH-1 receptor is expressed, human and primates express both MCH-1 and MCH-2 receptors (Genomics (2002), 79, 785-792). Originally, the MCH-1 receptor was considered a valuable target for the treatment of obesity as MCH promotes feeding behaviour in rodents (Nature (1996), 380, 243-247). Recently however, it was shown that MCH-1 antagonism produces anxiolytic and antidepressant profiles in rodents (Nat. Med. (2002) 8, 825-830; Neuropharmacology (2004), 46, 457-467; Neuropsychopharmacology (2005), in press). Thus, it is currently generally accepted that MCH receptors, particularly the MCH-1 receptor, are a good target for the treatment of affective spectrum disorders (Eur. J. Neuroscience (2000) 12, 1194-1216).

MCH-1 receptor mRNA and protein are distributed in various hypothalamic nuclei including the paraventricular nucleus and several limbic structures all implicated in the regulation of emotion ad stress (Eur. J. Neuroscience (2000) 12, 1194-1216). In addition, dense labelling is detected in the nucleus accumbens shell (J. Comp. Neurol. (2001) 435, 26-40). Injection of MCH directly into the paraventricular nucleus has been found to increase plasma adrenocorticotropic hormone (ACTH) and to alter sleep architecture (Verret et al. 2003, BMC Neurosci 4:19). Injection of MCH into the nucleus accumbens shell, in which MCH-1 receptor is abundant, increased immobility in a forced swim test in rats, suggesting increased depressive behavior (Soc. Neurosci. Abstr. (2004) 763.9). Moreover, Borowsky et al. (Nat. Med. (2002) 8, 825-830) reported the MCH-1 antagonist, SNAP-7941, exhibited antidepressant- and axiolytic-like affects in rodents tests, supporting a role for MCH-1 receptor in depression and anxiety.

BACKGROUND PRIOR ART

A large number of companies is now actively pursuing the development of MCH-1 antagonists and a wide range of structural types have been reported in a number of patent publications, mostly in relation to the regulation of food intake and energy expenditure (Expert Opin. Ther. Patents (2005) 15(10)). The majority of reported MCH-antagonists incorporate a basic centre and two (hetero)aromatic parts, joined by linkers. WO 2003/033480, WO 2003/033476 and WO 2005/05042541 (Glaxo Group Limited), WO 2004/024702 (Boehringer Ingelheim Pharma GMBH & Co. KG) and WO 2005/103039 (Neurocrine Biosciences Inc.) disclose different bicyclic heterocycles, such as thienopyrimid-4-one-, benzopyrimid-4-one- and ftalimide-derivatives, for use as MCH-1 antagonists. WO 2003/097047 and WO 2005/040157 (Eli Lilly and Company) and WO 2005/070925 (Aventis Pharma Deutschland GmbH) report different aromatic 5-membered ring heterocycles, such as oxazole- and oxadiazolederivatives, for use as MCH-1 antagonists. WO 2004/011438 and WO 2005/070898 (Aventis Pharma Deutschland GMBH) disclose diaryl-substituted cyclic urea derivatives as MCH-1 antagonist.

WO 2005/085200 (Banyu Pharmaceutical Co., Ltd) discloses pyridinone, pyrimidinone and pyridazinone-derivatives for use as MCH-1 antagonists. The compounds according to the invention differ from the compounds according to WO 2005/085200 in the nature of the core, in the nature of the substitution pattern and in the nature of the substituents. In particular the substituent (D) on the 3-position in our application differs from the substituent in the 4-position of WO 2005/085200 as the latter comprises a linker which is 2 atoms long, whereas the backbone of said linker in our application is at least 3 atoms (carbon and heteroatoms) long.

WO 98/11075 (Du Pont) discloses pyrazinones and triazinones and derivatives thereof as corticotropin releasing factor (CRF) antagonists. Although is has been found that MCH also induces corticotrophin-releasing factor (CRF) release from hypothalamic explants, an effect that is sensitive to blockade by an MCH-1 receptor antagonist (J. Neuroendrocinol. (2003) 15, 268-2729), no direct evidence is present that such effect is present for the compounds of WO 98/11075, which should then not be taken as a starting point for the development of MCH-1 antagonists. The compounds of the invention differ from the compounds of WO 98/11075 by the substitution pattern of the pyrazinone core.

DESCRIPTION OF THE INVENTION

It is the object of the present invention to provide compounds with a binding affinity towards melanin-concentrating (MCH) receptors, in particular towards MCH-1 receptors, in particular as an antagonist.

This goal was achieved by a novel substituted pyrazinone derivative according to the general Formula (I)

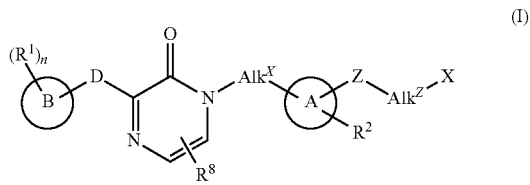

a pharmaceutically acceptable acid or base addition salt thereof, a stereochemically isomeric form thereof, an N-oxide form thereof or a quaternary ammonium salt thereof, wherein A is phenyl or a heterocyclic radical selected from the group of indolinyl, indazolyl, quinolinyl, furanyl, thiophenyl, chromenyl and pyridinyl;

B is a radical selected from the group of phenyl; biphenyl; naphthyl; cyclohexyl; cyclohexenyl; a heterocyclic radical selected from the group of azetidinyl, pyrrolyl, pyrazolyl, imidazolyl, pyridinyl, pyrimidinyl, pyrazinyl, pyridazinyl, pyrrolidinyl, imidazolidinyl, pyrazolidinyl, piperidinyl, homopiperidiyl, diazepyl, morpholinyl, thiomorpholinyl, piperazinyl, imidazolidinyl, imidazolinyl, pyrazolinyl, 1,2,3,4-tetrahydro-isoquinolinyl, indolyl and isoindolyl; and a radical composed of a benzo-radical fused to a heterocyclic 5- or 6-membered ring containing 1 or 2 hetero-atoms selected from the group of N, O and S;

D is a radical of formula $Y^2$-$Alk^Y$-$Y^1$ or $Y^2$-$Alk^Y$-$Pir^1$; provided that the backbone of D is at least 3 atoms long;

Z, $Y^1$, $Y^2$ are each, independently from each other, selected from the group of a covalent bond; —O—; —$NR^7$—; —S—; —SO—; and —$SO_2$; wherein $R^7$ is hydrogen or alkyl;

$Alk^X$, $Alk^Y$, $Alk^Z$ are each, independently from each other, a covalent bond or a saturated or unsaturated $C_{1-6}$ hydrocarbon radical, wherein one or more hydrogen atoms in each moiety $Alk^Y$ and $Alk^Z$ may optionally be replaced by a radical selected from the group of halo, cyano, hydroxy, amino, oxo and formyl;

$R^1$ represents one or more substituents selected from the group of hydrogen; halo; cyano; hydroxy; amino; oxo; nitro; thio; formyl; alkyl; alkyloxy; alkylcarbonyl; and mono- or di(alkyl)amino;

n is an integer, equal to 0, 1, or 2;

$R^2$ represents one or more substituents selected from the group of hydrogen; halo; cyano; hydroxy; amino; oxo; formyl; alkyl; alkyloxy; alkyloxyalkyl; mono- and di(alkyl)amino; mono- and di(alkyl)aminoalkyl; alkylcarbonyl; alkyloxycarbonyl; aminocarbonyl; mono- and di(alkyl) aminocarbonyl; $Het^1$; and $Het^1$carbonyl;

X is a radical selected from the group of $NR^3R^4$ and $Pir^2$;

$R^3$, $R^4$ each independently from each other, selected from the group of hydrogen; alkyl; alkylcarbonyl; $NR^aR^b$ and (C=O)$NR^aR^b$, wherein each of $R^a$ and $R^b$ is independently selected from alkyl, aryl and alkylaryl; aryl; aryloxy; $Het^2$; and alkyl substituted with one or more radicals selected from the group of $NR^aR^b$ and (C=O)$NR^aR^b$, wherein each of $R^a$ and $R^b$ is independently selected from alkyl, aryl and alkylaryl; aryl; alkyloxy; alkyloxycarbonyl; alkylsulphonyl; aryloxy and $Het^2$;

$R^8$ represents one or more substituents selected from the group of hydrogen, halo, cyano, hydroxy, amino, oxo, carboxy, alkyl, alkyloxy, alkylcarbonyl, mono or dialkylamino, nitro, thio, aryl, heteroaryl and formyl;

$Pir^1$ is a radical selected from the group of azetidinyl, pyrrolidinyl, piperidinyl, homopiperidiyl, 2H-pyrrolyl, pyrrolinyl, imidazolidinyl, pyrazolinyl and piperazinyl;

$Pir^2$ is a radical selected from the group of azetidinyl, pyrrolyl, pyrazolyl, imidazolyl, pyridinyl, pyrimidinyl, pyrazinyl, pyridazinyl, pyrrolidinyl, imidazolidinyl, pyrazolidinyl, piperidinyl, homopiperidiyl, diazepyl, morpholinyl, thiomorpholinyl, piperazinyl, imidazolidinyl, imidazolinyl, pyrazolinyl, 1,2,3,4-tetrahydroisoquinolinyl, indolyl and isoindolyl; wherein each Pir-radical is optionally substituted by one or more radicals selected from the group of hydrogen, halo, hydroxy, oxo, amino, aminocarbonyl, alkyl, alkyloxy, alkylcarbonyl, alkyloxycarbonyl, phenyl; and $NR^5R^6$, wherein $R^5$ and $R^6$ are independently from each other, selected from the group of hydrogen, alkyl, alkylcarbonyl, alkyloxycarbonyl and alkylsulphonyl;

$Het^1$ is pyrrolidinyl;

$Het^2$ is pyridinyl;

aryl is naphthalenyl or phenyl, each optionally substituted with 1, 2 or 3 substituents, each independently from each other, selected from the group of halo, cyano, hydroxy, amino, alkylamino, alkyloxyalkylamino, oxo, carboxy, nitro, thio, formyl and alkyloxy; and alkyl is a saturated, straight or branched hydrocarbon radical having from 1 to 6 carbon atoms; or is a saturated, cyclic hydrocarbon radical having from 3 to 7 carbon atoms; or is a saturated, cyclic hydrocarbon radical having from 3 to 7 carbon atoms attached to a saturated, straight or branched hydrocarbon radical having from 1 to 6 carbon atoms; each radical may optionally be substituted on one or more carbon atoms with one or more radicals selected from the group of halo, cyano, hydroxy, amino, oxo, carboxy, nitro, thio and formyl.

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, a stereochemically isomeric form thereof, an N-oxide form thereof or a quaternary ammonium salt thereof.

The invention also relates to the use of a compound according to the invention as a medicament and for the preparation of a medicament for the prevention and/or treatment of a disorder or disease responsive to antagonism of the MCH receptor, in particular to antagonism of the MCH-1 receptor.

In particular, the invention relates to the use of a compound according to the invention for the preparation of a medicament for the prevention and/or treatment of psychiatric disorders, including but not limited to anxiety, eating disorders, mood disorders, such as bipolar disorders and depression, psychoses, such as schizophrenia, and sleeping disorders. Additionally, the compound can be used for treating obesity, diabetes, sexual disorders and neurological disorders.

The compounds according to the invention, in particular according to Formula (I), may also be suitable as add-on treatment or combination treatment and/or prophylaxis in the above listed diseases, in particular for the prevention and/or treatment of psychiatric disorders, in combination with antidepressants, anxiolytics and/or antipsychotics which are currently available or in development or which will become available in the future, to improve efficacy and/or onset of action. This is evaluated in rodent models in which antidepressants, anxiolytics and/or antipsychotics are shown to be active. For example, compounds are evaluated in combination with antidepressants, anxiolytics and/or antipsychotics for attenuation of stress-induced hyperthermia.

The invention therefore also relates to the use of the compounds according to the invention in combination with one or more other compounds selected from the group of antidepressants, anxiolytics and antipsychotics, to a pharmaceutical composition comprising the compounds according to the invention and one or more other compounds selected from the group of antidepressants, anxiolytics and antipsychotics, as well as to a process for the preparation of such pharmaceutical compositions.

The invention also relates to the use of the compounds according to the invention in combination with one or more other compounds selected from the group of lipid-lowering compounds for the prevention and/or treatment of obesity, to a pharmaceutical composition comprising the compounds according to the invention and one or more other compounds selected from the group of lipid-lowering compounds, as well as to a process for the preparation of such pharmaceutical compositions.

DETAILED DESCRIPTION OF THE INVENTION

In a preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein A is phenyl.

In another preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein B is selected from the group of phenyl, 1,2,3,4-tetrahydro-isoquinolinyl, chromanyl and benzodioxolyl.

In another preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $Y^1$ and $Y^2$ are each, independently from each other, selected from the group of a covalent bond; —O—; —NR$^7$—; and —S—; wherein $R^7$ is hydrogen or alkyl.

In further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $Y^1$ is selected from the group of —NR$^7$—; and —S—; wherein $R^7$ is hydrogen or alkyl.

In further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein $Y^2$ is selected from the group of a covalent bond and —O—.

In further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Pir$^1$ is selected from the group of pyrrolidinyl and piperidinyl.

In further preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Alk$^Y$ is selected from the group of —CH$_2$CH$_2$— and —CH$_2$CH$_2$CH$_2$—, wherein one or more hydrogen atoms in each moiety Alk$^Y$ and Alk$^Z$ may optionally be replaced by an oxo-radical.

Preferably, the backbone of D is 3, 4 or 5 atoms long. In the framework of this application, with "backbone of D" is meant the consecutive sequence of atoms (carbon, sulfur, nitrogen and oxygen) that bridges the distance between on the one hand, the pyrazinone-core moiety in Formula (I) and on the other hand, the B-moiety in Formula (I).

Most preferably, D is selected from the group of —CH$_2$CH$_2$NH—, —OCH$_2$CH$_2$NH—, and —OCH$_2$CH$_2$CH$_2$NH—.

In another preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Z is selected from the group of a covalent bond; —O— and —NH—.

In another preferred embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Alkz is selected from the group of a covalent bond, —CH═CHCH$_2$—, —CH$_2$CH$_2$—, —CH$_2$CH$_2$CH$_2$— and —CH$_2$CH$_2$CH$_2$CH$_2$—.

In yet another embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Pir$^2$ is selected from the group of pyrrolidinyl; piperidinyl; morpholinyl; and piperazinyl; wherein each Pir-radical is optionally substituted by one or more radicals selected from the group of hydrogen, hydroxy; and NR$^5$R$^6$, wherein R$^5$ and R$^6$ are independently from each other, selected from the group of hydrogen, alkyl, alkylcarbonyl, alkyloxycarbonyl and alkylsulphonyl.

In yet another embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein Alk$^x$ is selected from the group of a covalent bond, —CH$_2$— and —CH$_2$CH$_2$—. Preferably, Alk$^x$ is a covalent bond.

In yet another embodiment, the invention relates to a compound according to general Formula (I), a pharmaceutically acceptable acid or base addition salt thereof, a stereochemically isomeric form thereof, an N-oxide form thereof or a quaternary ammonium salt thereof, wherein A is phenyl or a heterocyclic radical selected from the group of indolinyl, indazolyl, quinolinyl, chromenyl and pyridinyl;

D is a radical of formula Y$^2$-Alk$^Y$-Y$^1$ or Y$^2$-Alk$^Y$-Pir$^1$; provided that the backbone of D is at least 3 atoms long;

B is selected from the group of phenyl, 1,2,3,4-tetrahydro-isoquinolinyl, chromanyl and benzodioxolyl;

Z, Y$^1$, Y$^2$ are each, independently from each other, selected from the group of a covalent bond; —O—; —NR$^7$—; and —S—; wherein R$^7$ is hydrogen or alkyl;

Alk$^X$, Alk$^Y$, Alk$^Z$ are each, independently from each other, a covalent bond or a saturated or unsaturated C$_{1-6}$ hydrocarbon radical; wherein one or more hydrogen atoms in each moiety Alk$^Y$ and Alk$^Z$ may optionally be replaced by an oxo-radical;

R$^1$ represents one or more substituents selected from the group of halo and alkyloxy;

n is an integer, equal to 0, 1, or 2;

R$^2$ represents one or more substituents selected from the group of hydrogen; halo; alkyl; alkyloxy; alkyloxyalkyl; alkylcarbonyl; alkyloxycarbonyl; and amino-carbonyl;

X is a radical selected from the group of NR$^3$R$^4$ and Pir$^2$;

R$^3$, R$^4$ each independently from each other, selected from the group of alkyl; alkylcarbonyl and alkyl substituted with one or more radicals selected from the group of mono- or di(alkyl)amino, aryl and Het$^2$;

R$^8$ is hydrogen;

Pir$^1$ is a radical selected from the group of pyrrolidinyl and piperidinyl;

Pir$^2$ is a radical selected from the group of pyrrolidinyl, piperidinyl, morpholinyl, and piperazinyl; wherein each Pir-radical is optionally substituted by one or more radicals selected from the group of hydrogen, hydroxy and NR$^5$R$^6$, wherein R$^5$ and R$^6$ are independently from each other, selected from the group of hydrogen, alkyl, alkylcarbonyl, alkyloxycarbonyl and alkylsulphonyl;

Het$^2$ is pyridinyl; and aryl is phenyl.

In the framework of this application, alkyl is a straight or branched saturated hydrocarbon radical having from 1 to 6 carbon atoms; or is a cyclic saturated hydrocarbon radical having from 3 to 7 carbon atoms; or is a cyclic saturated hydrocarbon radical having from 3 to 7 carbon atoms attached to a straight or branched saturated hydrocarbon radical having from 1 to 6 carbon atoms; wherein each radical may optionally be substituted on one or more carbon atoms with one or more radicals selected from the group of halo, cyano, hydroxy, amino, oxo, carboxy, nitro, thio and formyl. Preferably, alkyl is methyl, ethyl, propyl, isopropyl, butyl, tert-butyl, cyclopropyl, cyclopentyl, cyclohexyl, cyclohexylmethyl and cyclohexylethyl.

In the framework of this application, aryl is naphthalenyl or phenyl, each optionally substituted with 1, 2 or 3 substituents, each independently from each other, selected from the group of halo, cyano, hydroxy, amino, alkylamino, alkyloxyalkylamino, oxo, carboxy, nitro, thio, formyl and alkyloxy.

In the framework of this application, heteroaryl refers to an optionally substituted monocyclic or bicyclic unsaturated, aromatic ring system containing at least one heteroatom selected independently from N, O or S. Examples of "heteroaryl" may be, but are not limited to thienyl, pyridyl, thiazolyl, isothiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl and thiadiazolyl, benzoimidazolyl, benzooxazolyl, benzothiazolyl, tetrahydrotriazolopyridyl, tetrahydrotriazolopyrimidinyl, benzofuryl, thionaphtyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridyl, oxazolopyridyl, thiazolopyridyl, pyridyl, imidazopyridazinyl, oxazolopyridazinyl, thiazolopyridazinyl, pteridinyl, furazanyl, benzotriazolyl, pyrazolopyridinyl, purinyl and the like. Each heteroaryl-radical may optionally be substituted with 1, 2 or 3 substituents, each independently from each other, selected from the group of halo, cyano, hydroxy, amino, alkylamino, alkyloxyalkylamino, oxo, carboxy, nitro, thio, formyl and alkyloxy.

In the framework of this application, halo is a substituent selected from the group of fluoro, chloro, bromo and iodo and polyhaloalkyl is a straight or branched saturated hydrocarbon radical having from 1 to 6 carbon atoms or a cyclic saturated hydrocarbon radical having from 3 to 7 carbon atoms, wherein one or more carbon atoms is substituted with one or more halo-atoms. Preferably, halo is bromo, fluoro or chloro and preferably, polyhaloalkyl is trifluoromethyl.

In the framework of this application, with "compounds according to the invention" is meant a compound according to the general Formula (I), a pharmaceutically acceptable acid or base addition salt thereof, a stereochemically isomeric form thereof, an N-oxide form thereof or a quaternary ammonium salt thereof.

The pharmaceutically acceptable acid addition salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said acid addition salt forms can be converted into the free base form by treatment with an appropriate base.

The compounds according to Formula (I) containing acidic protons may also be converted into their therapeutically active non-toxic metal or amine addition salts forms (base addition salts) by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate acid.

Quaternary ammonium salts of compounds according to Formula (I) defines said compounds which are able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has a positively charged nitrogen. Pharmaceutically acceptable counterions include chloro, bromo, iodo, trifluoroacetate and acetate ions.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g. of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

The invention also comprises derivative compounds (usually called "pro-drugs") of the pharmacologically-active compounds according to the invention, which are degraded in vivo to yield the compounds according to the invention. Prodrugs are usually (but not always) of lower potency at the target receptor than the compounds to which they are degraded. Pro-drugs are particularly useful when the desired compound has chemical or physical properties that make its administration difficult or inefficient.

For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and Drugs, 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$ alkyl, phenyl, benzyl or one of the following groups:

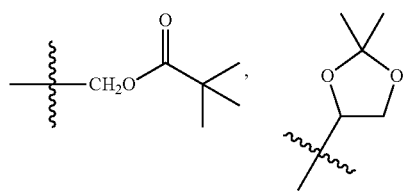

Amidated groups include groups of the formula —CONR$^y$R$^z$, wherein R$^y$ is H, C$_{1-6}$ alkyl, phenyl or benzyl and R$^z$ is —OH, H, C$_{1-6}$ alkyl, phenyl or benzyl. Compounds according to the invention having an amino group may be derivatised with a ketone or an aldehyde such as formaldehyde to form a Mannich base. This base will hydrolyze with first order kinetics in aqueous solution.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. In particular, when hydrogen is mentioned, it is understood to refer to $^1$H, $^2$H, $^3$H and mixtures thereof; when carbon is mentioned, it is understood to refer to $^{11}$C, $^{12}$C, $^{13}$C, $^{14}$C and mixtures thereof; when nitrogen is mentioned, it is understood to refer to $^{13}$N, $^{14}$N, $^{15}$N and mixtures thereof; when oxygen is mentioned, it is understood to refer to $^{14}$O, $^{15}$O, $^{16}$O, $^{17}$O, $^{18}$O and mixtures thereof; and when fluor is mentioned, it is understood to refer to $^{18}$F, $^{19}$F and mixtures thereof.

The compounds according to the invention therefore also comprise compounds with one or more isotopes of one or more element, and mixtures thereof, including radioactive compounds, also called radiolabelled compounds, wherein one or more non-radioactive atoms has been replaced by one of its radioactive isotopes. By the term "radiolabelled compound" is meant any compound according to Formula (I), an N-oxide form, a pharmaceutically acceptable addition salt or a stereochemically isomeric form thereof, which contains at least one radioactive atom. For example, compounds can be labelled with positron or with gamma emitting radioactive isotopes. For radioligand-binding techniques (membrane receptor assay), the $^3$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Preparation

The compounds according to the invention can generally be prepared by a succession of steps, each of which is known to the skilled person. In particular, the compounds can be prepared according to the following synthesis methods.

Scheme 1: General synthesis scheme 1

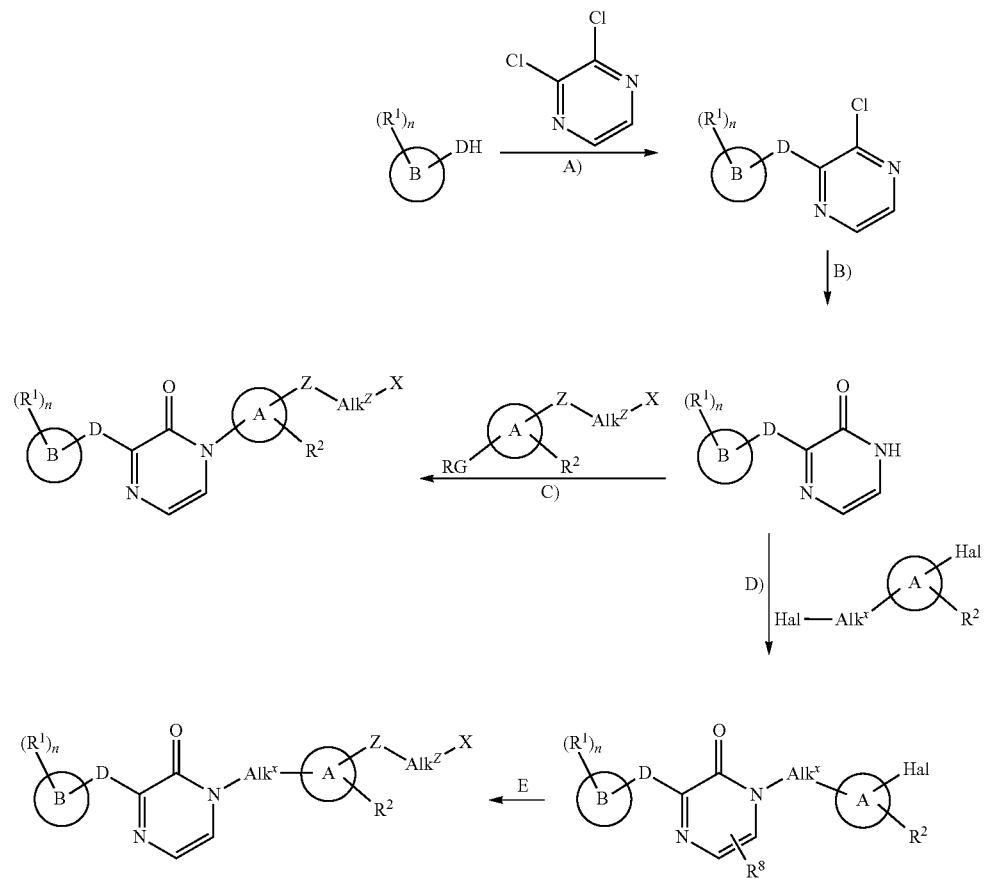

In step A) a dichloropyrazine is reacted in a suitable solvent, such as acetonitrile, either by conventional heating under reflux or by microwave irradiation, for a period of time to ensure the completion of the reaction, typically 20 minutes at 180° C. under microwave conditions, in the presence of a suitable base, such as NaOH, LiOH and NaH which can be used when $Y^1$=O or S, or bases like 1,8-diazabicyclo(5.4.0.) undec-7-ene (DBU), $K_2CO_3$ and NaOH, which can be used when $Y^1$=NR$^7$ and Pir$^1$.

The resulting intermediate compound is converted in step B) to a pyrazinone in a suitable solvent, such as dimethylsulfoxide, either by conventional heating under reflux or by microwave irradiation, for a period of time to ensure the completion of the reaction, typically 30 minutes at 150° C. under microwave conditions, in the presence of a suitable aqueous base, such as NaOH, or a suitable aqueous acid, such as hydrochloric acid.

In step C), the resulting intermediate compound is reacted with the intermediate compound shown, wherein the RG-moiety is suitable for being substituted, such as Br or $C_1$, $CF_3CO_2$ or $B(OH)_2$ The reaction is performed in a suitable solvent such as dichloroethane, in the presence of a copper compound, such as CuI or Cu(AcO)$_2$, either in catalytic or equivalent amount; in the presence of a suitable ligand, such as pyridine or N,N'-dimethylethylenediamine and at a convenient temperature, either by conventional heating under reflux or under microwave irradiation, for a period of time to ensure the completion of the reaction. Additionally, an inorganic base such as $K_3PO_4$ can be added to the reaction. In all steps A), B) and C), all variables are as defined in Formula (I), unless otherwise specified.

In step D), the resulting intermediate compound is reacted with the intermediate compound shown, wherein the Hal moiety means Cl, Br or I, suitable for being substituted. The reaction is performed in a suitable solvent such as AcCN, in the presence of an inorganic base such as $K_2CO_3$, heating under reflux or under microwave irradiation, for a period of time to ensure the completion, typically in microwave at 150° C. for 20 min.

Step E) includes a typical transformation of the Hal (Cl, Br or I) moiety to obtain the desired final compounds, by methods well described in literature and known to the skilled person.

Said intermediate compound in scheme 1 may be prepared according to scheme 1a or 1b.

Scheme 1a (for Z = O)

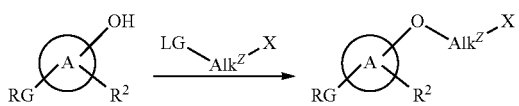

Scheme 1b (for A = pyridinyl)

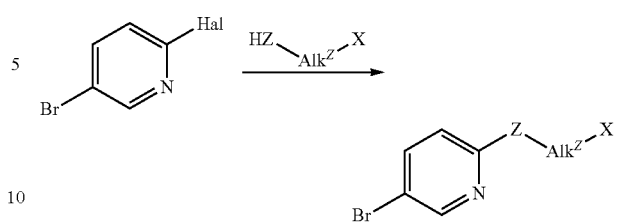

When LG is a suitable leaving group such as Br, Cl, I or an ester of sulfonic acid, the alkylation reaction can be carried out in an aprotic polar solvent, such as for instance acetonitrile, DMF or dioxane; in the presence of an inorganic or organic base, such as $K_2CO_3$, $Na_2CO_3$, $Cs_2CO_3$, NaH, $Et_3N$, BTPP or PS-TBD; at a convenient temperature, such as 150° C. under microwave irradiation or reflux temperature using con-ventional heating. In the case where LG=OH, a Mitsunobu-type reaction can be used to obtain the desired compounds in a suitable aprotic solvent, such as tetrahydrofurane, in the presence of a phosphine ligand, such as triphenylphosphine and a diazoderivative, such as diethyl azodicarboxylate; either while stirring at room temperature or by heating at 80° C. using traditional heating or microwave irradiation for a suitable period of time. All variables are as defined in Formula (I), unless otherwise specified; for example, A should not be 2-pyridinyl; in the latter case scheme 1b should be used. The RG-moiety is suitably a halogen, such as Br or $C_1$, $CF_3CO_2$ or $B(OH)_2$.

2-Pyridyl and 2-quinolyl intermediates can be prepared following scheme 1b by nucleophilic aromatic substitution in a suitable solvent, such as tetrahydrofurane or DMF, in the presence of a suitable base, such as NaH or DBU, by heating at a convenient temperature, such as 150° C. under microwave irradiation or reflux temperature under traditional heating, for a period of time that allows the completion of the reaction. Additionally, a metal catalyst, such as palladium, and a suitable ligand, such as 2-(ditert-buthylphosphino)biphenyl, can be added to enhance the reaction.

The compound according to the invention may also be prepared according to the general synthesis scheme 2.

Scheme 2: General synthesis scheme 2.

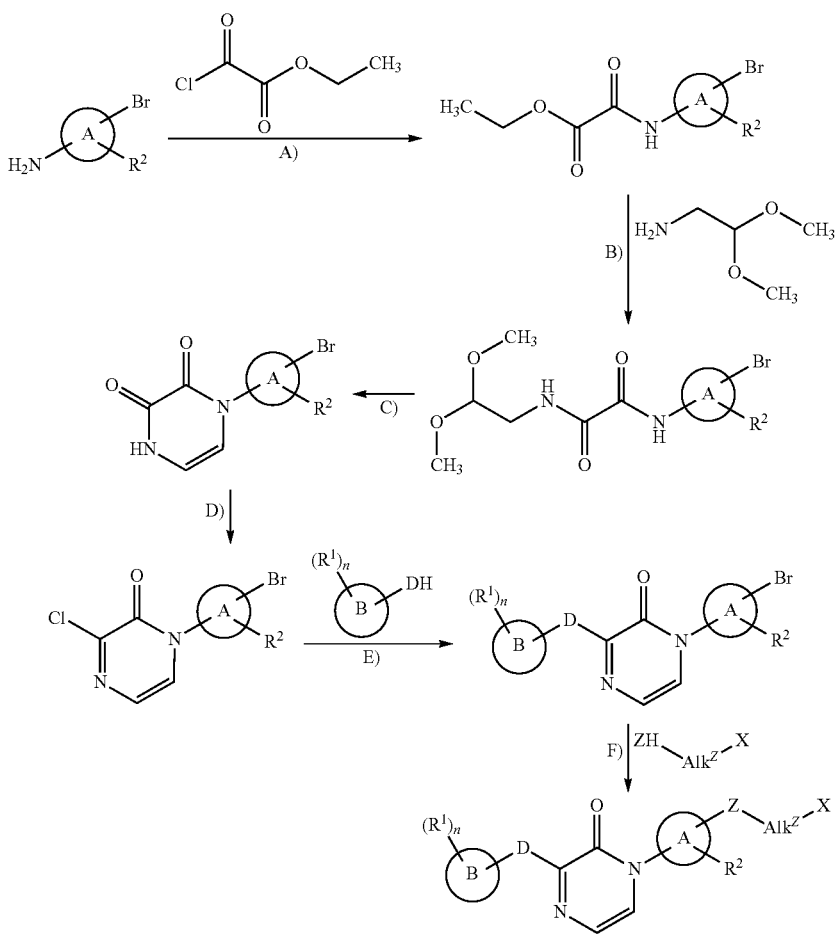

Z = $NR^7$ and Z = covalent bond only if $Alk^Z$ is also a covalent bond

In step A) a primary amino derivative can be reacted with an alkyl chloroglyoxalate, such as methyl chloroglyoxalate, in a suitable aprotic solvent, such as dichloromethane, in the presence of a suitable base, such as triethylamine.

The methoxy group of the resulting intermediate is substituted in step B) with aminoacetaldehyde dimethylacetal; alternatively other aminoacetaldehyde analogues can be also used, such as aminoacetaldehyde diethylacetal; in a suitable solvent, such as 2-propanol, by heating at a suitable temperature, such as 170° C. using microwave irradiation or reflux temperature using traditional heating, for a suitable period of time.

The resulting intermediate was cyclizated in step C) in a suitable solvent, such as tetrahydrofurane, in the presence of a suitable aqueous acid, such as hydrochloric acid, either by conventional heating under reflux or by microwave irradiation, for a period of time to ensure the completion of the reaction, typically 10 minutes at 150° C. under microwave conditions.

The resulting pyrazindione intermediate was transformed in chloropyrazinone in step D) in a suitable aprotic solvent, such as dichloroethane, using a suitable chlorinating agent, such as phosphorus oxychloride (POCl$_3$) and heating at a suitable temperature for a suitable period of time that allows the completion of the reaction, either using microwave irradiation or traditional heating. Alternatively a suitable base, such as triethylamine can be added to enhance the reaction.

The chlorine atom of the resulting intermediate can be substituted in step E) in a suitable solvent, such as acetonitrile, dimethylformamide or N-methylpyrrolidone (NMP), in the presence of a suitable base, such as K$_2$CO$_3$ or PS-TBD, heating for a suitable period of time, either using microwave irradiation at, for instance, 170° C. or traditional heating at reflux temperature, that allow the completion of the reaction. The resulting intermediate is converted in step F) to the compound shown by a Hartwig-Bushwald type reaction with an amino group, in a suitable solvent, such as dioxane or toluene, in the presence of a suitable base, such as sodium tert-buthoxyde, a metal based catalyst, such as Pd$_2$(dba)$_3$, and a suitable ligand, such as 2-(di-tertbuthylphosphino)biphenyl, by heating for a suitable period of time, either using microwave irradiation at, for instance, 170° C. or traditional heating at reflux temperature, that allows the completion of the reaction.

The compound according to the invention may also be prepared according to the general synthesis scheme 3.

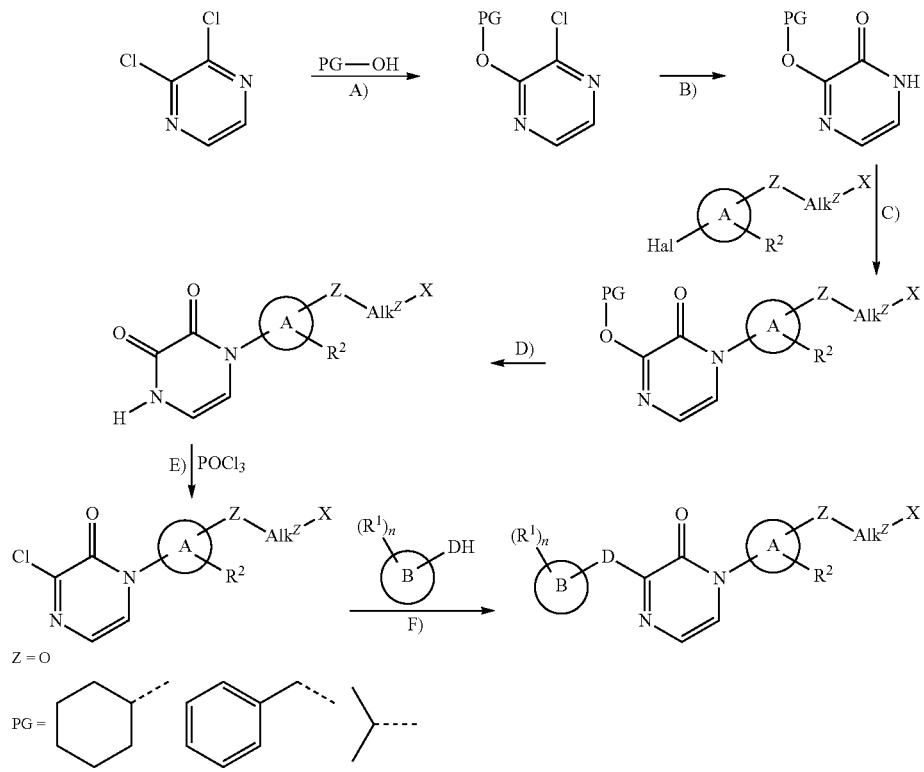

Scheme 3: General synthesis scheme 3.

In step A) a dichloropyrazine is reacted in a suitable solvent, such a tetrahydrofurane with an alcohol that support an appropriate protecting group, such a cyclohexyl, benzyl or isopropyl groups, in the presence of a suitable base, such as NaH, and heated to reflux for a period of time to ensure the completion of the reaction.

The resulting intermediate compound is converted in step B) to a pyrazinone in a suitable solvent, such as dimethylsulfoxide, either by conventional heating under reflux or by microwave irradiation, for a period of time to ensure the completion of the reaction, typically 30 minutes at 150° C. under microwave conditions, in the presence of a suitable aqueous base, such as NaOH.

In step C), the resulting intermediate compound is reacted with the intermediate compound shown, wherein the RG-moiety is suitable for being substituted, such as Br or C$_1$, CF$_3$CO$_2$ or B(OH)$_2$ The reaction is performed in a suitable solvent such as dichloroethane, in the presence of a copper compound, such as CuI or Cu(AcO)$_2$, either in catalytic or equivalent amount; in the presence of a suitable ligand, such as pyridine or N,N'-dimethylethylenediamine and at a convenient temperature, either by conventional heating under reflux or under microwave irradiation, for a period of time to ensure the completion of the reaction. Additionally, an inorganic base such as K$_3$PO$_4$ can be added to the reaction.

The protecting group of the resulting intermediate is deprotected in step D) in a suitable solvent, such as tetrahydrofurane, in the presence of a suitable aqueous acid, such as hydrochloric acid, by heating to reflux for a period of time to ensure the completion of the reaction.

The resulting pyrazindione intermediate was transformed in chloropyrazinone in step E) in a suitable aprotic solvent, such as dichloroethane, using a suitable chlorinating agent, such as phosphorus oxychloride (POCl$_3$) and heating at a suitable temperature for a suitable period of time that allows the completion of the reaction, either using microwave irradiation or traditional heating. Alternatively a suitable base, such as triethylamine can be added to enhance the reaction.

The chlorine atom of the resulting intermediate can be substituted in step F) in a suitable solvent, such as acetonitrile, dimethylformamide or N-methylpyrrolidone (NMP), in the presence of a suitable base, such as K$_2$CO$_3$ or PS-TBD, heating for a suitable period of time, either using microwave irradiation at, for instance, 170° C. or traditional heating at reflux temperature, that allows the completion of the reaction.

The chlorine atom in step F can be used to form a C—C bond as well, via a coupling reaction, using a suitable solvent, such as dimethylformamide, in the presence of PdCl$_2$(PPh$_3$)$_2$ and CuI as catalyst, and in the presence of a suitable base such as DIPEA, stirring at room temperature, for a period of time to ensure the completion of the reaction.

Pharmacology

The compounds according to the invention, in particular compounds according to Formula (I), the pharmaceutically acceptable acid or base addition salts thereof, a stereochemically isomeric form thereof, an N-oxide form thereof or a quaternary ammonium salt thereof, have surprisingly been shown to have a binding affinity towards the MCH-receptor, in particular towards the MCH-1 receptor, in particular as an antagonist.

In view of their above mentioned potency, the compounds according to the invention are suitable for the prevention and/or treatment of diseases where antagonism of the MCH-receptor, in particular antagonism of the MCH-1 receptor is of therapeutic use. In particular, the compounds according to the invention may be suitable for treatment and/or prophylaxis of psychiatric disorders, including but not limited to:

anxiety, including but not limited to agoraphobia; generalized anxiety; compulsion; obsessive-compulsive disorder; panic disorder; social phobia; and stress, such a post-traumatic stress;

attention deficit/hyperactivity disorder;

autism;

dysthymia;

eating disorder, including but not limited to anorexia; binge eating; and bulimia nervosa;

impulse control disorder;

mental retardation, including but not limited to fragile X syndrome;

mood disorder, including but not limited to agitation; bipolar disorder, such as bipolar affective disorder, bipolar disorder (I), bipolar disorder (II), hypomania and mania; depression, such as major depression and suicidal depression; seasonal mood disorder; and suicide;

premenstrual syndrome, including but not limited to dysphoria;

psychosis, including but not limited to aggressiveness; drug-induced psychosis; schizoaffective disorder; schizophrenia, such as delusion, catatonia, catatonic schizophrenia, disorganized schizophrenia, paranoid schizophrenia, residual schizophrenia and schizophreniform disorder; and dyssomnia, such as secondary dyssomnia;

sleep disorder, including but not limited to circadian rhythm disorder; hypersomnia; insomnia; narcolepsy and sleep apnea;

stuttering; and violence.

Additionally, the compound can be used for treating sexual disorders, neurological disorders, and most in particular obesity and diabetes.

The invention therefore relates to a compound according to the general Formula (I), a pharmaceutically acceptable acid or base addition salt thereof, a stereochemically isomeric form thereof, an N-oxide form thereof or a quaternary ammonium salt thereof, for use as a medicine.

The invention also relates to the use of a compound according to the invention for the preparation of a medicament for the prevention and/or treatment of diseases where antagonism of the MCH-receptor, in particular antagonism of the MCH-1 receptor is of therapeutic use.

The invention also relates to the use of a compound according to the invention for the preparation of a medicament for the prevention and/or treatment of anxiety, eating disorders, mood disorders, such as bipolar disorders and depression, psychoses, such as schizophrenia, and sleeping disorders. Additionally, the compound can be used for treating sexual disorders and neurological disorders, and in particular obesity and diabetes.

Combination Treatments

The compounds according to the invention, in particular according to Formula (I) may be co-administered as add-on treatment and/or prophylaxis in the above listed diseases.

With Antidepressants, Anxiolytics and/or Antipsychotics.

In particular the compounds according to the invention, in particular according to Formula (I) may be co-administered in combination with antidepressants, anxiolytics and/or antipsychotics which are currently available or in development or which will become available in the future, in particular to improve efficacy and/or onset of action. It will be appreciated that the compounds of the present invention and the other agents may be present as a combined preparation for simultaneous, separate or sequential use for the prevention and/or treatment of depression and/or anxiety. Such combined preparations may be, for example, in the form of a twin pack. It will also be appreciated that the compounds of the present invention and the other agents may be administered as separate pharmaceutical compositions, either simultaneously or sequentially.

The invention therefore relates to a pharmaceutical composition according to the invention, characterized in that is comprises further one or more other compounds selected from the group of antidepressants, anxiolytics and antipsychotics.

Suitable classes of antidepressant agents include norepinephrine reuptake inhibitors, selective serotonin reuptake inhibitors (SSRI's), monoamine oxidase inhibitors (MAOI's), reversible inhibitors of monoamine oxidase (RIMA's), serotonin and noradrenaline reuptake inhibitors (SNRI's), noradrenergic and specific serotonergic antidepressants (NaSSA's), corticotropin releasing factor (CRF) antagonists, α-adrenoreceptor antagonists and atypical antidepressants.

Suitable examples of norepinephrine reuptake inhibitors include amitriptyline, clomipramine, doxepin, imipramine, trimipramine, amoxapine, desipramine, maprotiline, nortriptyline, protriptyline, reboxetine and pharmaceutically acceptable salts thereof.

Suitable examples of selective serotonin reuptake inhibitors include fluoxetine, fluvoxamine, paroxetine, sertraline and pharmaceutically acceptable salts thereof. Suitable examples of monoamine oxidase inhibitors include isocarboxazid, phenelzine, tranylcypromine, selegiline and pharmaceutically acceptable salts thereof.

Suitable examples of reversible inhibitors of monoamine oxidase include moclobemide and pharmaceutically acceptable salts thereof.

Suitable examples of serotonin and noradrenaline reuptake inhibitors include venlafaxine and pharmaceutically acceptable salts thereof.

Suitable atypical antidepressants include bupropion, lithium, nefazodone, trazodone, viloxazine, sibutramine and pharmaceutically acceptable salts thereof.

Other suitable antidepressants include adinazolam, alaproclate, amineptine, amitriptyline/chlordiazepoxide combination, atipamezole, azamianserin, bazinaprine, befuraline, bifemelane, binodaline, bipenamol, brofaromine, bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, monirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, tofenacin, tofisopam, toloxatone, tomoxetine, veralipride, viqualine, zimelidine and zometapine and pharmaceutically acceptable salts thereof, and St. John's wort herb, or Hypericum perforatum, or extracts thereof.

Suitable classes of anti-anxiety agents include benzodiazepines and 5-$HT_{1A}$ receptor agonists or antagonists, especially 5-$HT_{1A}$ partial agonists, corticotropin releasing factor (CRF) antagonists, compounds having muscarinic cholinergic activity and compounds acting on ion channels. In addition to benzodiazepines, other suitable classes of anti-anxiety agents are nonbenzodiazepine sedative-hypnotic drugxs such as zolpidem; mood-stabilizing drugs such as clobazam, gabapentin, lamotrigine, loreclezole, oxcarbamazepine, stiripentol and vigabatrin; and barbiturates.

Suitable antipsychotic agents are selected from the group consisting of acetophenazine, in particular the maleate salt; alentemol, in particular the hydrobromide salt; alpertine; azaperone; batelapine, in particular the maleate salt; benperidol; benzindopyrine, in particular the hydrochloride salt; brofoxine; bromperidol; butaclamol, in particular the hydrochloride salt; butaperazine; carphenazine, in particular the maleate salt; carvotroline, in particular the hydrochloride salt; chlorpromazine; chlorprothixene; cinperene; cintriamide; clomacran, in particular the phosphate salt; clopenthixol; clopimozide; clopipazan, in particular the mesylate salt; cloroperone, in particular the hydrochloride salt; clothiapine; clothixamide, in particular the maleate salt; clozapine; cyclophenazine, in particular the hydrochloride salt; droperidol; etazolate, in particular the hydrochloride salt; fenimide; flucindole; flumezapine; fluphenazine, in particular the decanoate, enanthate and/or hydrochloride salts; fluspiperone; fluspirilene; flutroline; gevotroline, in particular the hydrochloride salt; halopemide; haloperidol; iloperidone; imidoline, in particular the hydrochloride salt; lenperone; loxapine; mazapertine, in particular the succinate salt; mesoridazine; metiapine; milenperone; milipertine; molindone, in particular the hydrochloride salt; naranol, in particular the hydrochloride salt; neflumozide, in particular the hydrochloride salt; ocaperidone; olanzapine; oxiperomide; penfluridol; pentiapine, in particular the maleate salt; perphenazine; pimozide; pinoxepin, in particular the hydrochloride salt; pipamperone; piperacetazine; pipotiazine, in particular the palmitate salt; piquindone, in particular the hydrochloride salt; prochlorperazine, in particular the edisylate salt; prochlorperazine, in particular the maleate salt; promazine, in particular the hydrochloride salt; quetiapine; remoxipride; risperidone; rimcazol, in particular the hydrochloride salt; seperidol, in particular the hydrochloride salt; sertindole; setoperone; spiperone; sulpiride; thioridazine; thiothixene; thorazine; tioperidone, in particular the hydrochloride salt; tiospirone, in particular the hydrochloride salt; trifluoperazine, in particular the hydrochloride salt; trifluperidol; triflupromazine; ziprasidone, in particular the hydrochloride salt; and mixtures thereof.

Lipid-Lowering Compounds

The compounds according to the invention, in particular according to Formula (I) may also be used in conjunction with other lipid-lowering agent, thus leading to a so-called combination lipid-lowering therapy for the treatment of obesity. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors, CB-1 antagonists, cholesterol absorption inhibitors such as ezetimibe, and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such "HMG-CoA reductase inhibitors" are, for example, lovastatin, simvastatin, fluvastatin, pravastatin, rivastatin, and atorvastatin.

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetylcoenzyme A, catalyzed by the enzyme HMG-CoA synthase Any HMG-CoA reductase gene expression inhibitor may be used as the second compound in the combination therapy aspect of this invention. These agents may be HMG-CoA reductase trancription inhibitors that block the transcription of DNA or translation inhibitors that prevent translation of mRNA coding for HMG-CoA reductase into protein. Such inhibitors may either affect trancription or translation directly or may be biotransformed into compounds having the above-mentioned attributes by one or more enzymes in the cholesterol biosynthetic cascade or may lead to accumulation of a metabolite having the above-mentioned activities.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL.

Any ACAT inhibitor may be used as the second compound in the combination therapy aspect of this invention. The term "ACAT inhibitor" as used herein, unless oth-erwise stated, refers to a compound which inhibits the intracellular esterification of dietary cholesterol by the enzyme acyl CoA:cholesterol acyltransferase.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable acid or base addition salt thereof, a stereochemically isomeric form thereof, an N-oxide form thereof or a quaternary ammonium salt thereof.

The compounds according to the invention, in particular the compounds according to Formula (I), the pharmaceutically acceptable acid or base addition salt thereof, a stereochemically isomeric form thereof, an N-oxide form thereof or a quaternary ammonium salt thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. Since the compounds according to the invention are potent orally administrable dopamine antagonists, pharmaceutical compositions comprising said compounds for administration orally are especially advantageous.

As already mentioned, the invention also relates to a pharmaceutical composition comprising the compounds according to the invention and one or more other com-pounds selected from the group of antidepressants, anxiolytics, antipsychotics and lipid-lowering agents as well as to the use of such a composition for the manufacture of a medicament.

Depending on the mode of administration, the pharmaceutical composition will include from about 0.05 weight % (weight %=percent by weight) to about 99 weight %, more particular, from about 0.10 weight % to about 99 weight %, of the compounds of the invention, all percentages by weight being based on the total weight of the composition. When the pharmaceutical composition comprises the compounds according to the invention and one or more other compounds selected from the group of antidepressants, anxiolytics, antipsychotics and lipid-lowering agents, both the compounds according to the invention and the one or more other compounds may be present in a concentration from about 0.05 weight % (weight %=percent by weight) to about 99 weight %, more particular, from about 0.10 weight % to about 99 weight %, all percentages by weight being based on the total weight of the composition. For example, the weight ratio of the compounds according to the invention to the one or more other compounds may be in the range of 0.05/0.94 to 0.94/0.05, more in particular 0.10/0.89 to 0.89/0.10, and any number therein between.

The following examples are intended to illustrate but not to limit the scope of the present invention.

Experimental Part

Hereinafter, "THF" means tetrahydrofuran, "DMF" means N,N-dimethylformamide, "EtOAc" means ethyl acetate, "DME" means 1,2-dimethoxyethane, "DCE" means 1,2-dichloroethane, "DIPE" means diisopropylether, "DMSO" means dimethylsulfoxide. "PS-TBD" is polymer-supported TBD and "PS—NCO" is polymer-supported isocyanate.

Microwave assisted reactions were performed in a single-mode reactor: Emrys™ Optimizer microwave reactor (Personal Chemistry A.B., currently Biotage). Description of the instrument can be found in www.personalchemistry.com. And in a multimode reactor: MicroSYNTH Labstation (Milestone, Inc.). Description of the instrument can be found in www.milestonesci.com.

A. Preparation of the Intermediate Compounds

Example A1 a) Preparation of Intermediate Compound 1

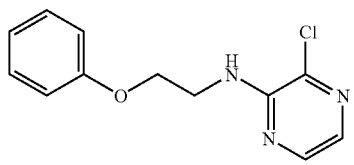

Reaction in microwave oven. A mixture of 2-phenoxyethanamine (0.010 mol), 2,3-dichloropyrazine (0.012 mol) and 1,8-diazabicyclo(5.4.0.)undec-7-ene (DBU) (0.012 mol) in $CH_3CN$ (20 ml) was heated for 20 minutes at 180° C. The solvent was evaporated. The residue was purified by short open column chromatography over silica gel (eluent: $CH_2Cl_2$). The product fractions were collected and the solvent was evaporated. Yield: 2.5 g of intermediate compound 1 (quantitative yield; used in next reaction step, without further purification).

b) Preparation of Intermediate Compound 2

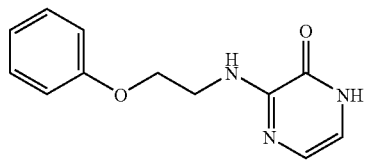

Reaction in microwave oven. A mixture of intermediate compound 1 (0.0092 mol) in NaOH (10 ml; 50%) and DMSO (10 ml) was heated for 30 minutes at 150° C. The reaction mixture was cooled to 0° C. EtOAc and water were added at 0° C. The organic layer was separated, dried ($Na_2SO_4$), filtered through Dicalite and the filtrate's solvent was evaporated. The residue was lyophilized, then purified by short open column chromatography over silica gel (eluent: $CH_2Cl_2$/EtOAc 80/20; then $CH_2Cl_2$/2-propanone 50/50). The product fractions were collected and the solvent was evaporated. The residue was washed with diethyl ether and was subsequently dried. Yield: 0.92 g of intermediate compound 2 (43%).

Example A2

Preparation of Intermediate Compound 3

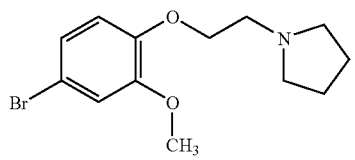

A mixture of 4-bromo-2-methoxyphenol (0.0246 mol), 2-hydroxyethylpyrrolidine (0.0492 mol) and triphenylphosphine (0.0492 mol) in THF (50 ml; dry) was stirred at 0° C. Diethylazodicarboxylate (0.0492 mol) was added at 0° C. in a microwave oven. The reaction mixture was stirred for 5 minutes at 100° C. An aqueous $Na_2CO_3$ solution was added. This mixture was extracted with EtOAc. The separated organic layer was dried ($Na_2SO_4$), filtered and the solvent was evaporated. The residue was 'caught' by addition of Amberlyst 15 (0.123 mol), subsequently 'released' by addition of $NH_3/CH_3OH$, subsequently purified by short open column chromatography over silica gel (eluent: $CH_2Cl_2$/($CH_3OH/NH_3$) 95/5). The product fractions were collected and the solvent was evaporated. Yield: 6.7 g of intermediate compound 3 (91%).

Example A3 a) Preparation of Intermediate Compound

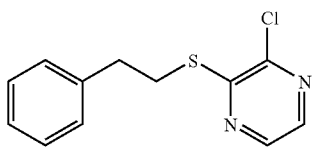

A mixture of NaH (0.0049 mol; 60%) in DCE (1.7 ml) was stirred at 0° C. A solution of 2-phenylethanethiol (0.0031 mol) in DCE (5.6 ml) was added portionwise at 0° C. The reaction mixture was stirred for 30 minutes at room temperature. A solution of 2,3-dichloropyrazine (0.0033 mol) in DCE (1.7 ml) was added and the resultant reaction mixture was heated for 10 minutes at 80° C. in a microwave oven. The mixture was filtered through Celite and the filter residue was washed with $CH_2Cl_2$. The filtrate's solvent was evaporated. The residue was purified by short open column chromatography over silica gel (eluent: $CH_2Cl_2$/heptane 1/1, then pure $CH_2Cl_2$). The product fractions were collected and the solvent was evaporated. Yield: 0.5 g of intermediate compound 4 (72%).

b) Preparation of Intermediate compound 5

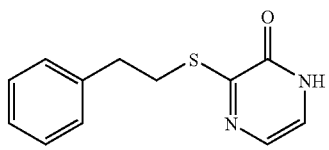

Reaction in microwave oven. A mixture of intermediate compound 4 (0.0023 mol) in NaOH (4 l; 50%) and DMSO (4 ml) was stirred for 30 minutes at 150° C. Water was added. EtOAc was added. The organic layer was separated, dried ($Na_2SO_4$), filtered and the solvent was evaporated. The residue was purified using a Sep-Pak fitted with 10 g of silica gel in a manifold under vacuum (eluent: $CH_2Cl_2$). The product fractions were collected and the solvent was evaporated. Yield: 0.060 g of intermediate compound 5 (12%).

Example A4

Preparation of Intermediate Compound 6

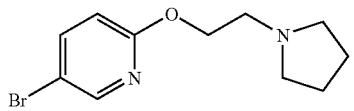

2-Hydroxyethylpyrrolidine (0.0030 mol) was added to NaH (0.0020 mol; 60%) in 1,2-dimethoxyethane (2 ml), stirred at 0° C. The reaction mixture was stirred for 15 minutes at room temperature. 5-Bromo-2-chloropyridine (0.0010 mol) was added. The reaction mixture was heated for 10 minutes at 150° C. in a microwave oven. A 10% aqueous $NH_4Cl$ solution was added. This mixture was extracted with EtOAc. The separated organic layer was dried ($Na_2SO_4$), filtered and the solvent was evaporated. The residue was purified by column chromatography using a Sep-Pak fitted with 10 g of silica gel in a manifold (eluent: $CH_2Cl_2$/($CH_3OH/NH_3$) 98/2 and 96/4). The product fractions were collected and the solvent was evaporated. Yield: 0.197 g of intermediate compound 6 (73%).

Example A5 a) Preparation of Intermediate Compound 7

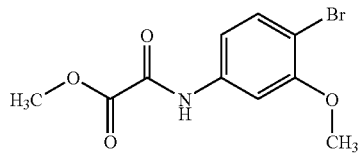

A solution of methyl chloroglyoxalate (0.0593 mol) in $CH_2Cl_2$ (50 ml) was added por-tionwise to a mixture of 4-bromo-3-methoxybenzenamine (0.0494 mol) and $Et_3N$ (0.0741 mol) in $CH_2Cl_2$ (50 ml), stirred at 0° C. The resultant reaction mixture was stirred for 24 hours at room temperature. A saturated aqueous $NaHCO_3$ solution was added. The organic layer was separated, dried ($Na_2SO_4$), filtered and the solvent was evaporated. The residue was treated with diethyl ether, subsequently filtered off and dried. Yield: 12.8 g of intermediate compound 7 (91%).

b) Preparation of Intermediate Compound 8

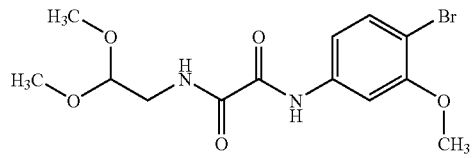

Reaction in microwave oven. A mixture of intermediate compound 7 (0.0444 mol; 2×6.4 g) and aminoacetaldehyde dimethylacetal (0.0666 mol; 2×3.6 g) in 2-propanol (95 ml; 2×47.5 ml) was heated for 15 minutes at 170° C. The precipitate was filtered off, washed with 2-propanol and diethyl ether, subsequently dried. Yield: 13.5 g of intermediate compound 8 (84%).

c) Preparation of Intermediate Compound 9

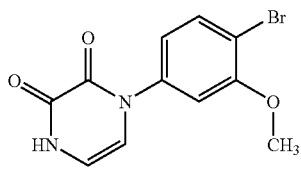

Reaction in microwave oven. A mixture of intermediate compound 8 (0.0373 mol; 2×6.75 g) in HCl (21 ml; 2×10.5 ml; 2N) and THF (98 ml; 2×49 ml) was heated for minutes at 150° C. The reaction mixture was extracted with $CH_2Cl_2$. The separated organic layer was dried ($Na_2SO_4$), filtered and the solvent evaporated. The residue was washed with diethyl ether, subsequently dried. Yield: 7.97 g of intermediate compound 9 (72%).

d) Preparation of Intermediate Compound 10

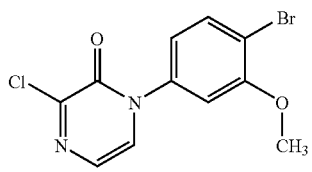

A mixture of intermediate compound 9 (0.0255 mol; 7×1.08 g), $POCl_3$ (0.0767 mol; 7×1 ml) and $Et_3N$ (0.0511 mol; 7×1 ml) in DCE (228 ml; 7×32.5 ml) was stirred for minutes at 150° C. A saturated aqueous $Na_2CO_3$ solution was added. The organic layer was separated, dried ($Na_2SO_4$), filtered and the solvent evaporated. The residue was purified by short open column chromatography over silica gel (eluent: $CH_2Cl_2$/EtOAc 90/10). The product fractions were collected and the solvent was evaporated. Yield: 3.9 g of intermediate compound 10 (49%).

e) Preparation of Intermediate Compound 11

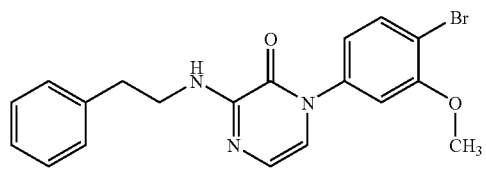

A mixture of intermediate compound 10 (0.0031 mol), phenethylamine (0.0063 mol) and $K_2CO_3$ (0.0063 mol) in $CH_3CN$ (15 ml) was stirred for 20 minutes at 170° C. in a microwave oven. $CH_2Cl_2$ was added. The precipitate was filtered off and the filtrate's solvent was evaporated. The residue was purified by short open column chromatography over silica gel (eluent: CH$_2$Cl$_2$). The product fractions were collected and the solvent was evaporated. Yield: 1 g of intermediate compound 11 (83%).

Example A6 a) Preparation of Intermediate Compound 12

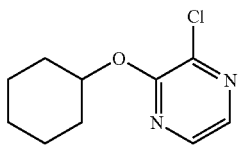

A solution of cyclohexanol (0.05 mol) in 1,2-dimethoxyethane (15 ml) was added dropwise to a mixture of NaH (0.05 mol; 60%) in 1,2-dimethoxyethane (10 ml), stirred at 0° C. The mixture was stirred for 10 minutes at 0° C. in a microwave oven. A solution of 2,3-dichloropyrazine (0.034 mol) in 1,2-dimethoxyethane (25 ml) was added and the resultant reaction mixture was stirred and refluxed for 30 minutes. Water was added. This mixture was extracted with EtOAc. The separated organic layer was dried (Na$_2$SO$_4$), filtered and the solvent evaporated. Yield: 9.0 g of intermediate compound 12 (used in next reaction step, without further purification).

b) Preparation of Intermediate Compound 13

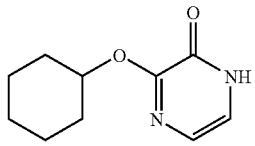

A mixture of intermediate compound 12 (0.034 mol) in NaOH (25 ml) and DMSO (25 ml) was heated for 90 minutes at 120° C. Water was added. This mixture was extracted with EtOAc. A saturated aqueous NH$_4$Cl solution was added to the separated organic phase. This mixture was extracted with EtOAc. The combined organic layers were dried (Na$_2$SO$_4$), filtered and the solvent was evaporated. The residue was purified by short open column chromatography over silica gel (eluent: CH$_2$Cl$_2$ and EtOAc). The product fractions were collected and the solvent was evaporated. The residue was treated with DIPE, subsequently filtered off and dried. Yield: 2.4 g of intermediate compound 13 (36%).

c) Preparation of Intermediate Compound 14

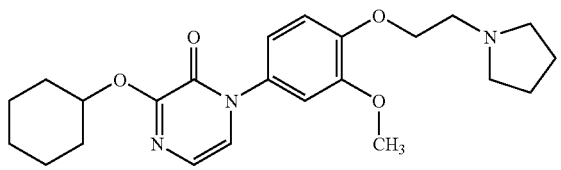

A mixture of intermediate compound 13 (0.012 mol), intermediate compound 3 (0.015 mol), CuI (0.012 mol), N,N'-dimethylethylenediamine (0.024 mol) and K$_3$PO$_4$ (0.024 mol) in dioxane/DMF (35 ml; 5/1) was heated for 15 minutes at 180° C. in a microwave oven. CH$_2$Cl$_2$ was added. The solid was filtered off through a Celite pad and to the filtrate, a 32% NH$_3$ solution was added. The organic layer was separated, washed with brine, dried (Na$_2$SO$_4$), filtered and the solvent was evaporated. The residue was purified by short open column chromatography over silica gel. The product fractions were collected and the solvent was evaporated. Yield: 4.2 g of intermediate compound 14 (85%).

d) Preparation of Intermediate Compound 15

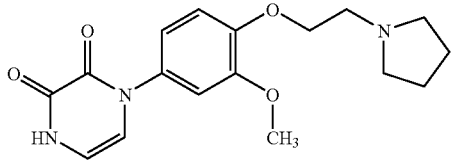

A mixture of intermediate compound 14 (0.010 mol) in HCl (10 ml; 2N) and THF (30 ml) was heated for 2 hours at 100° C. A saturated aqueous NaHCO$_3$ solution was added. This mixture was extracted with CH$_2$Cl$_2$. The layers were separated. The organic layer was dried (Na$_2$SO$_4$), filtered, to give filtrate (*). The aqueous layer was evaporated and the solid was washed with methanol to give filtrate (**). The filtrates (*) and (**) were combined, and the solvent evaporated. The residue was purified by short open column chromatography over silica gel (eluent: CH$_2$Cl$_2$/CH$_3$OH 90/10; then: CH$_2$Cl$_2$/(CH$_3$OH/NH$_3$) 80/20). The product fractions were collected and the solvent was evaporated. The residue was treated with diethyl ether, subsequently filtered off and dried. Yield: 1.74 g of intermediate compound 15 (53%).

e) Preparation of Intermediate Compound 16

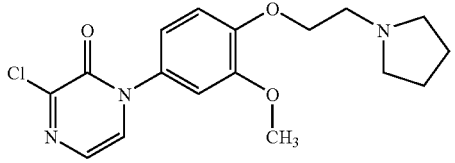

POCl$_3$ (0.015 mol) was added to a mixture of intermediate compound 15 (0.005 mol) and Et$_3$N (0.010 mol) in DCE (30 ml) and the resultant reaction mixture was heated for 10 minutes at 150° C. in the microwave oven. The solid was filtered off through Celite and washed with CH$_2$Cl$_2$. The filtrate was treated with a saturated aqueous Na$_2$CO$_3$ solution, subsequently dried (Na$_2$SO$_4$), filtered and the solvent was evaporated. The residue was purified by short open column chromatography over silica gel (eluent: CH$_2$Cl$_2$/CH$_3$OH 95/5 and CH$_2$Cl$_2$/(CH$_3$OH/NH$_3$) 95/5). The product fractions were collected and the solvent was evaporated. The residue was treated with DIPE, filtered off and dried. Yield: 0.960 g of intermediate compound 16 (55%).

f) Preparation of Intermediate Compound 17

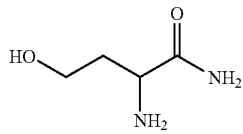

A mixture of alpha-amino-gamma-butyrolactone hydrobromide (1 g, 0.0055 mol) and MeOH/NH$_3$7N (7 ml) was stirred in microwave at 100° C. for 10 min. The solvent was concentrated in vacuo to yield intermediate compound 17 as a colourless oil, which was used in next reaction step without further purification.

g) Preparation of Intermediate Compound 18

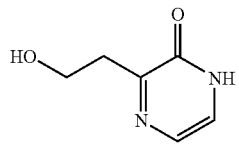

To a solution of intermediate compound 17 (5.5 mmol), glyoxal (0.8 g, 5.5 mmol) in MeOH (5 ml) cooled to −10° C. was added NaOH 12.5 N (0.550 ml, 6.9 mmol). The reaction mixture was stirred at room temperature for 48 hours. Subsequently HCl 12N (0.575 ml, 6.9 mmol) was added. The reaction mixture was stirred at room temperature for 45 min. Portions of NaHCO$_3$ solid was added to get pH aprox. 6. The reaction was filtered off. The filtrate was evaporated. The residue was treated with MeOH/CH$_2$Cl$_2$. A precipitate appears which was filtered off (impurities). The filtrate was evaporated to yield: 0.350 g of intermediate compound 18 (45%).

h) Preparation of Intermediate Compound 19

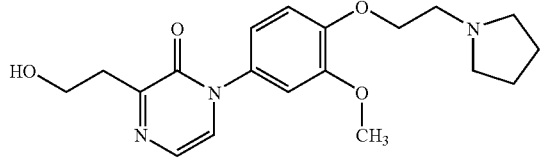

To a solution of intermediate compound 18 (0.405 g, 2.89 mmol) in dioxane:DMF 9:1 (7 ml) was added intermediate compound 3 (0.868 g, 2.89 mmol), CuI (0.578 g, 2.89 mmol), N,N'-dimethylethylenediamine (2.89 mmol) and K$_3$PO$_4$ (0.638 g, 2.89 mmol). The reaction mixture was heated at 175° C. under microwave irradiation for 30 min. NH$_4$OH aqueous and EtOAc were added. The mixture was extracted with EtOAc. The separated organic layer was dried (Na$_2$SO$_4$), filtered, and the solvent was evaporated. The residue was purified by automated chromatography over silica gel (eluent: CH$_2$Cl$_2$/MeOH(NH$_3$) 100 to 96:4. The desired fractions were collected and the solvent was evaporated to yield: 0.300 g of intermediate compound 19 (30%).

i) Preparation of Intermediate Compound 20

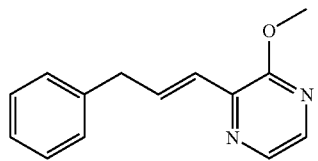

A mixture of 2-chloro-3-methoxypyrazine (0.300 g, 0.0028 mol), trans-3-phenylpropen-1-yl-boronic acid (0.336 g, 0.0028 mol), Pd(PPh$_3$)$_4$ (0.243 g, 0.00021 mol) in dioxane (3 ml) and NaHCO$_3$ aqueous saturated solution (1 ml) was heated in a microwave at 150° C. for 0.5 hours. The solvent was concentrated under reduced pressure. The crude was purified by flash chromatography in CH$_2$Cl$_2$ 100 to CH$_2$Cl$_2$ (MeOH(NH$_3$) 97:3 to yield 0.120 g of a colourless oil of intermediate compound 20.

j) Preparation of Intermediate Compound 21

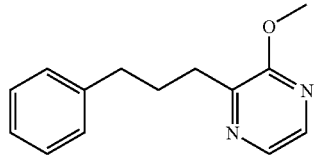

To a solution of intermediate compound 20 (0.120 g, 0.00053 mol) in MeOH (20 ml) was hydrogenated under H$_2$ atmosphere for 4 hours. using Palladium on Carbon as a catalyst (12 mg). The mixture was filtered off and the filtrate was concentrated to yield 100 mg of intermediate compound 21.

k) Preparation of Intermediate Compound 22

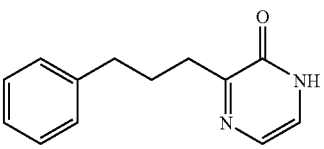

A solution of intermediate compound 21 (0.100 g, 0.00044 mol) in a mixture of HCl 6N (2 ml) and THF (1 ml) was heated in microwave at 140° C. for 20 minutes and for minutes more to get completion of the reaction. The mixture was concentrated and the resulting crude, intermediate compound 22, was used in next reaction step without further purification.

l) Preparation of Intermediate Compound 23

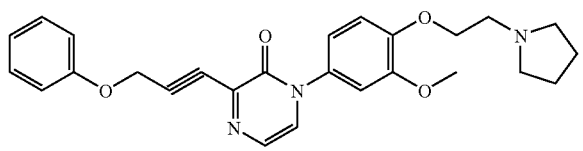

A mixture of intermediate compound 16 (0.170 g, 0.00048 mol), phenyl propargyl ether (0.062 ml, 0.00048 mol), PdCl$_2$ (PPh$_3$)$_2$ (24 mg, 0.034 mmol), CuI (5 mg, 0.024 mmol), DIPEA (0.173 ml, 0.00099 mol) in DMF (3 ml) was stirred under N$_2$ atmosphere in a seal tube at room temperature for 16 hours. Subsequently, an aqueous saturated solution of ClNH$_4$, and Et$_2$O was added. The organic phase was dried (Na$_2$SO$_4$) and evaporated. The resulting crude was purified by flash chromatography in SiO$_2$ (eluent: CH$_2$Cl$_2$/(CH$_3$OH/NH$_3$) 100/0 to 97/3) to yield 45 mg of a light yellow oil as intermediate compound 23.

m) Preparation of Intermediate Compound 24

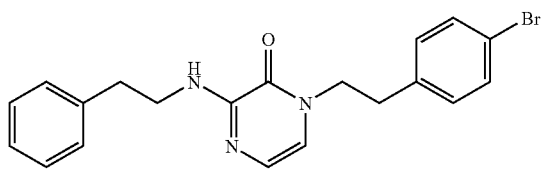

A mixture of intermediate compound 3-phenethylamino-1H-pyrazin-2-one (0.4 g, 0.0019 mol) (prepared according to the method described for intermediate compound 2), 4-bromophenethyl bromide (0.443 ml, 0.0029 mol), K$_2$CO$_3$ (0.401 g, 0.0029 mol) in AcCN (4 ml) was heated in microwave at 150° C. for 20 min. The solids were filtered off and washed with CH$_2$Cl$_2$. The filtrate was evaporated. The residue was purified by column chromatography. The desired fraction were collected and evaporated. The product was precipitated with DIPE affording 0.365 g of intermediate compound 24 (48%).

n) Preparation Intermediate Compound 25

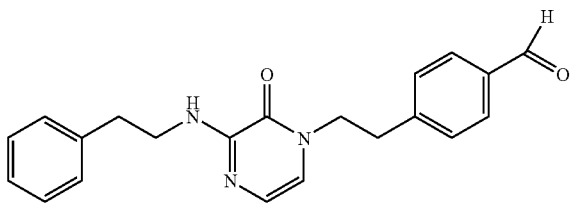

A mixture of intermediate compound 24 (0.365 g, 0.0009 mol), formylacetyl anhydride (0.137 ml, 0.0018 mol), PdCl$_2$(PPh$_3$)$_2$ (0.063 g, 0.09 mmol), triethylsilane (0.224 ml, 0.0014 mol), diisopropylethylamine (0.314 ml, 0.0018 mol) in AcCN (4 ml) was heated in microwave at 75° C. for 3 days. Subsequently, CH$_2$Cl$_2$ and NaHCO$_3$ (saturated aqueous solution) were added. The organic layer was separated, dried (Na$_2$SO$_4$) and the solvent evaporated. The residue was purified by column chromatography (eluents: CH$_2$Cl$_2$ and CH$_2$Cl$_2$/EtOAc 4:1) affording 0.244 g of intermediate compound 25 (78%).

B. Preparation of the Final Compounds

Example B1

Preparation of Final Compound 1-67

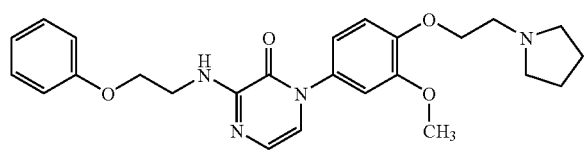

Reaction in microwave oven. A mixture of intermediate compound 2 (0.00043 mol), intermediate compound 3 (0.00052 mol), CuI (0.00043 mol), N,N'-dimethylethylenediamine (0.00086 mol) and K$_3$PO$_4$ (0.00086 mol) in dioxane/DMF (2 ml; 9/1) was heated for 20 minutes at 175° C. CH$_2$Cl$_2$ was added. The whole was filtered through Celite and the filtrate was treated with an aqueous NH$_4$Cl solution. The organic layer was separated, dried (Na$_2$SO$_4$), filtered and the solvent was evaporated. The residue was purified by column chromatography using a Sep-Pak fitted with 10 g of silica gel in a manifold (eluent: CH$_2$Cl$_2$/CH$_3$OH 95/5 and CH$_2$Cl$_2$/(CH$_3$OH/NH$_3$) 96/4). The product fractions were collected and the solvent was evaporated. The residue was precipitated as HCl salt (1:1) in EtOAc. The precipitate was filtered off and dried. Yield: 0.095 g of final compound 1-67 (45%).

Example B2

Preparation of Final Compound 2-04

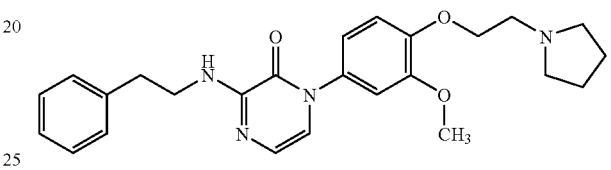

Reaction in microwave oven. A mixture of 3-phenethylamino-1H-pyrazin-2-one (0.00046 mol) (prepared according to the method described for intermediate compound 2), intermediate compound 3 (0.00055 mol), CuI (0.00046 mol), N,N'-dimethylethylenediamine (0.00092 mol) and K$_3$PO$_4$ (0.00092 mol) in dioxane/DMF (3.5 ml; 9/1) was heated for 20 minutes at 175° C. CH$_2$Cl$_2$ was added. The whole was filtered through Celite and the filtrate was treated with an aqueous NH$_4$Cl solution. The organic layer was separated, dried (Na$_2$SO$_4$), filtered and the solvent was evaporated. The residue was purified by column chromatography using a Sep-Pak fitted with 10 g of silica gel in a manifold (eluent: CH$_2$Cl$_2$/CH$_3$OH 100/0, 97.5/2.5, 95/5 and 90/10). The product fractions were collected and the solvent was evaporated. Yield: 0.13 g of final compound 2-04.

Example B3

Preparation of Final Compound 2-10

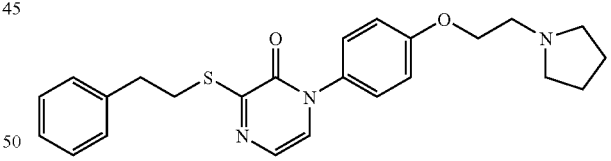

Reaction in microwave oven. A mixture of intermediate compound 5 (0.0002582 mol), 1-[2-(4-bromophenoxy)ethyl]pyrrolidine (0.0003099 mol), CuI (0.0002582 mol), N,N'-dimethylethylenediamine (0.0005164 mol) and K$_3$PO$_4$ (0.0005164 mol) in dioxane/DMF (2 ml; 9/1) was heated for 20 minutes at 175° C. CH$_2$Cl$_2$ was added. The mixture was filtered through Celite and the filtrate was treated with an aqueous NH$_4$Cl solution. The organic layer was separated, dried (Na$_2$SO$_4$), filtered and the solvent was evaporated. The residue was purified by column chromatography using a Sep-Pak fitted with 5 g of silica gel in a manifold (eluent: CH$_2$Cl$_2$/CH$_3$OH 100/0, 97.5/2.5, 95/5 and 90/10). The product fractions were collected and the solvent was evaporated. Yield: 0.035 g of final compound 2-10 (32%).

Example B4

Preparation of Final Compound 3-91

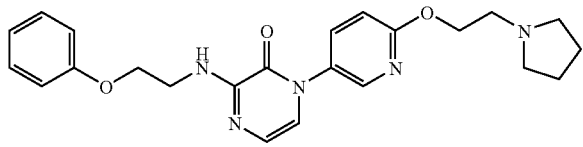

Reaction in microwave oven. A mixture of intermediate compound 2 (0.00030 mol), intermediate compound 6 (0.00036 mol), CuI (0.00030 mol), N,N'-dimethylethylenediamine (0.00060 mol) and $K_3PO_4$ (0.00060 mol) in dioxane/DMF (2 ml; 9/1) was heated for 20 minutes at 175° C. The solid was filtered off and washed with $CH_2Cl_2$. Subsequently, an aqueous $NH_4Cl$ solution was added. The organic layer was separated, dried ($Na_2SO_4$), filtered and the solvent was evaporated. The residue was purified by column chromatography using a Sep-Pak fitted with 10 g of silica gel in a manifold (eluent: $CH_2Cl_2/(CH_3OH/NH_3)$ 98/2 and 96/4). The product fractions were collected and the solvent was evaporated. The residue was treated with diethyl ether, filtered off and dried. Yield: 0.090 of final compound 3-91 (71%).

Example B5

Preparation of Final Compound 3-10

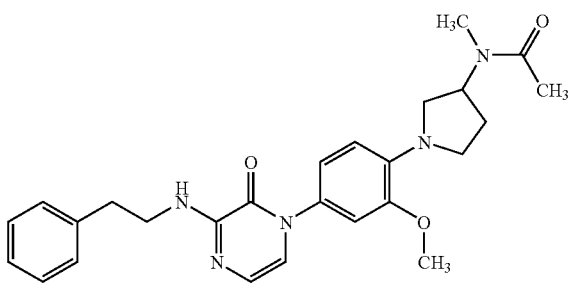

A mixture of intermediate compound 11 (0.00034 mol), N-methyl-N-3-pyrrolidinylacetamide (0.00069 mol), $Pd_2(dba)_3$ (0.000034 mol), [1,1'-biphenyl]-2-ylbis(1,1-dimethylethyl)phosphine (0.000068 mol) and 2-methyl-2-propanol, sodium salt (0.00085 mol) in toluene/$CH_3CN$ (2 ml; 4/1; deoxygenated) was stirred for 4 days at 90° C. $CH_2Cl_2$ was added. The precipitate was filtered off through Celite and the filtrate's solvent was evaporated. The residue was purified by column chromatography using a Sep-Pak fitted with 10 g of silica gel in a manifold (eluent: $CH_2Cl_2/(CH_3OH/NH_3)$ 98/2 and 96/4), then by HPLC. The product fractions were collected and the solvent was evaporated. Yield: 0.0553 g of final compound 3-10 (37%).

Example B6

Preparation of Final Compound 4-04

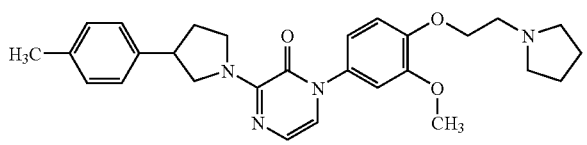

Reaction in microwave oven. 3-(4-methylphenyl)piperidine (0.00013 mol) and PSTBD (0.00017 mol) were added to a solution of intermediate compound 16 (0.000086 mol) in 1-methyl-2-pyrrolidinone (3 ml) and the reaction mixture was heated for 20 minutes at 170° C. PS-NCO (1 equiv) was added and the mixture was stirred for minutes at 20° C. The mixture was filtered and the filtrate was passed through a 'catch and release' SCX-2 (strong cation exchange resin) cartridge, washing with methanol, then with $CH_3OH/NH_3$. This phase was concentrated under $N_2$. The crude residue was further purified by HPLC. The product fractions were collected and the solvent was evaporated. Yield: 0.017 g of final compound 4-04.

Example B7

Preparation of Final Compound 2-07

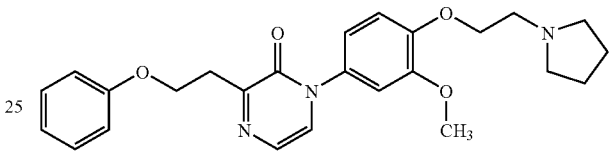

To a solution of potassium phenyltrifluoroborate (0.154 g, 0.83 mmol) in $CH_2Cl_2$ (2 ml) was added $Cu(OAc)_2$ (9 mg, 0.04 mmol), DMAP (10 mg, 0.084 mmol) and molecular sieves 4A. Then a solution of intermediate compound 19 (0.150 g, 0.42 mmol) in $CH_2Cl_2$ (2 ml) was added. The reaction mixture was stirred at room temperature for 16 h open to air. The reaction mixture was filtered off through celite in $CH_2Cl_2$. The filtrate was evaporated. The residue was purified by automated chromatography over silica gel (eluent: $CH_2Cl_2/(CH_3OH/NH_3)$ 100 to 97/3). The desired fractions were collected and the solvent was evaporated. The product was purified again by HPLC to yield: 0.010 g of final compound 2-07 (6%).

Example B8

Preparation of Final Compound 2-01

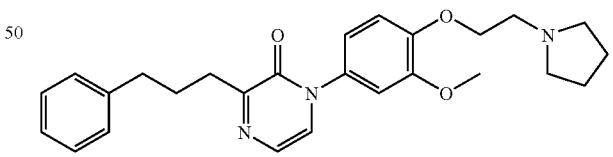

A mixture of intermediate compound 22 (0.00047 mol), intermediate compound 3 (0.0007 mol), CuI (0.00047 mol), N,N'-dimethylethylenediamine (0.00047 mol) and $K_3PO_4$ (0.00094 mol) in dioxane/DMF (2 ml; 9/1) was heated in microwave for 30 minutes at 175° C. The solvent was evaporated and the residue was purified by column chromatography with $SiO_2$ (eluent: $CH_2Cl_2/(CH_3OH/NH_3)$ 100/0 to 95/5). The product fractions were collected and the solvent was evaporated to yield: 0.020 g which were precipitated with DIPE/Heptane 2:1 to obtain 10 mg of a white solid of final compound 2-01.

Example B9

Preparation of Final Compound 2-08

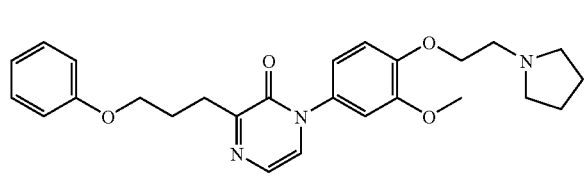

A solution of intermediate compound 23 (20 mg, 0.045 mmol) in MeOH was hydrogenated under $H_2$ pressure atmosphere (15 psi) and using Pd—C (4 mg) as a catalyst for 3 h. The mixture was filtered through celite and the solvent was evaporated. The residue was purified by column chromatography in $SiO_2$ (eluent: $CH_2Cl_2/(CH_3OH/NH_3)$ 100/0 to 97/3) to yield 10 mg of the final compound 2-08.

Example B10

Preparation of Final Compound 9-02

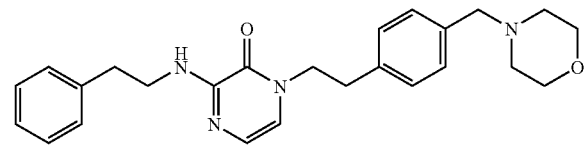

A mixture of intermediate compound 25 (0.122 g, 0.00035 mol), morpholine (0.046 ml, 0.00053 mol), sodium borohydride (0.112 g, 0.00053 mol) in 1,2-DCE (3 ml) was heated in microwave for 10 minutes at 80° C. Then $NH_4Cl$ (saturated aqueous solution) was added. The organic layer was separated, dried ($Na_2SO_4$) and the solvent evaporated. The residue was purified by column chromatography (eluents: $CH_2Cl_2/$MeOH 98/2 and 96/4). The desired fractions were collected and the solvent evaporated. The residue was precipitated with DIPE affording 85 mg of final compound 9-02 (58%).

Tables 1 to 9 list the compounds of Formula (I), which were prepared according to one of the above described examples.

TABLE 1

| Co. Nr. | Ex. Nr. | --$R^2$-- | --Z-- | --$Alk^Z$-- | --L-- | Salt/Descriptor |
|---|---|---|---|---|---|---|
| 1-01 | B5 | --H | (cb) | (cb) | pyrrolidine-NH-CH₃ | RS |
| 1-02 | B5 | --H | (cb) | (cb) | pyrrolidine-N(CH₃)C(O)CH₃ | RS |
| 1-03 | B5 | --H | (cb) | (cb) | pyrrolidine-N(CH₃)C(O)CH(CH₃)₂ | RS |
| 1-04 | B5 | --H | (cb) | (cb) | pyrrolidine-N(CH₃)C(O)OC(CH₃)₃ | RS |

TABLE 1-continued

| Co. Nr. | Ex. Nr. | --R² | --Z-- | --Alkᶻ-- | --L | Salt/Descriptor |
|---|---|---|---|---|---|---|
| 1-05 | B5 | --H | (cb) | (cb) | methanesulfonyl-N-methyl-(1-methylpyrrolidin-3-yl)amine | RS |
| 1-06 | B5 | --H | (cb) | (cb) | 4-(piperazin-1-yl) with NH | |
| 1-07 | B5 | --H | (cb) | (cb) | 4-isopropylpiperazin-1-yl | |
| 1-08 | B5 | --OCH₃ | (cb) | (cb) | 3-hydroxy-1-methylpyrrolidin-1-yl | RS |
| 1-09 | B5 | --OCH₃ | (cb) | (cb) | 3-(methylamino)-1-methylpyrrolidin-1-yl | RS |
| 1-10 | B5 | --OCH₃ | (cb) | (cb) | 3-(dimethylamino)-1-methylpyrrolidin-1-yl | RS |
| 1-11 | B5 | --OCH₃ | (cb) | (cb) | N-methyl-N-(1-methylpyrrolidin-3-yl)isobutyramide | RS |

TABLE 1-continued
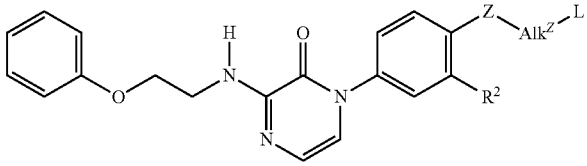
| Co. Nr. | Ex. Nr. | --R² | --Z-- | --Alkᶻ-- | --L | Salt/Descriptor |
|---|---|---|---|---|---|---|
| 1-12 | B5 | --OCH₃ | (cb) | (cb) | 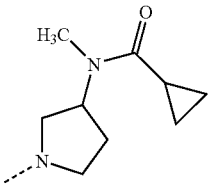 | RS |
| 1-13 | B5 | --OCH₃ | (cb) | (cb) | 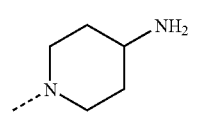 | |
| 1-14 | B5 | --OCH₃ | (cb) | (cb) | 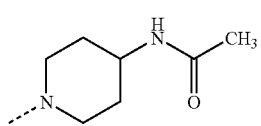 | |
| 1-15 | B5 | --OCH₃ | (cb) | (cb) | 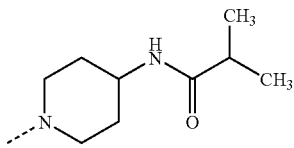 | |
| 1-16 | B1 | --H | (cb) |  | 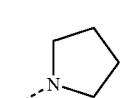 | |
| 1-17 | B1 | --OCH₃ | (cb) |  | 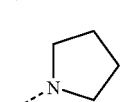 | (E) |
| 1-18 | B1 | --OCH₃ | (cb) |  | 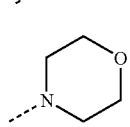 | (E) |
| 1-19 | B5 | --H | --NH-- | --CH₂CH₂-- | 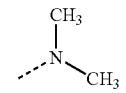 | |
| 1-20 | B5 | --H | --NH-- | --CH₂CH₂-- | 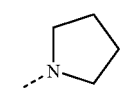 | |
| 1-21 | B5 | --H | --NH-- | --CH₂CH₂CH₂-- | 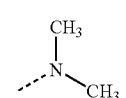 | |
| 1-22 | B5 | --H | --NH-- | --(C=O)CH₂-- | 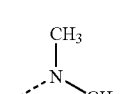 | |

TABLE 1-continued
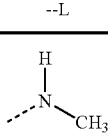
| Co. Nr. | Ex. Nr. | --R² | --Z-- | --Alk^Z-- | --L | Salt/ Descriptor |
|---|---|---|---|---|---|---|
| 1-23 | B1 | --H | --O-- | --CH₂—CH₂-- | 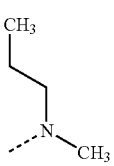 | |
| 1-24 | B1 | --H | --O-- | --CH₂CH₂-- | 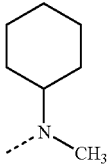 | |
| 1-25 | B1 | --H | --O-- | --CH₂CH₂-- | 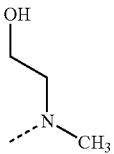 | |
| 1-26 | B1 | --H | --O-- | --CH₂CH₂-- | 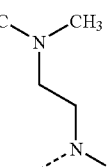 | |
| 1-27 | B1 | --H | --O-- | --CH₂CH₂-- | 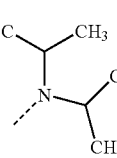 | |
| 1-28 | B1 | --H | --O-- | --CH₂CH₂-- | 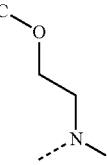 | |
| 1-29 | B1 | --H | --O-- | --CH₂CH₂-- | 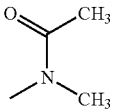 | |
| 1-30 | B1 | --H | --O-- | --CH₂CH₂-- | | |

TABLE 1-continued
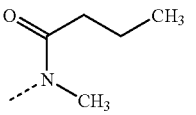
| Co. Nr. | Ex. Nr. | --R² | --Z-- | --Alk^Z-- | --L | Salt/Descriptor |
|---|---|---|---|---|---|---|
| 1-31 | B1 | --H | --O-- | --CH₂CH₂-- | 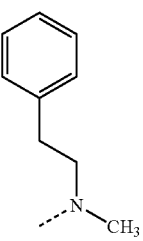 | |
| 1-32 | B1 | --H | --O-- | --CH₂CH₂-- | 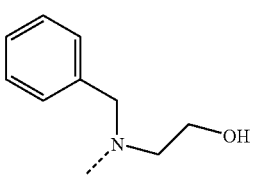 | |
| 1-33 | B1 | --H | --O-- | --CH₂CH₂-- | 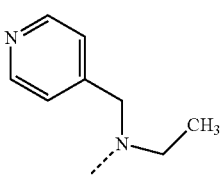 | |
| 1-34 | B1 | --H | --O-- | --CH₂CH₂-- | 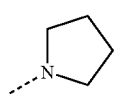 | |
| 1-35 | B1 | --H | --O-- | --CH₂CH₂-- | 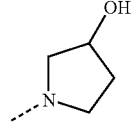 | |
| 1-36 | B1 | --H | --O-- | --CH₂CH₂-- | 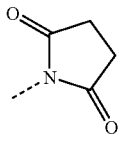 | RS |
| 1-37 | B1 | --H | --O-- | --CH₂CH₂-- | 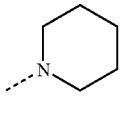 | |
| 1-38 | B1 | --H | --O-- | --CH₂CH₂-- | 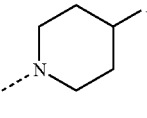 | |
| 1-39 | B1 | --H | --O-- | --CH₂CH₂-- |  | |

TABLE 1-continued

| Co. Nr. | Ex. Nr. | --R² | --Z-- | --Alk^Z-- | --L | Salt/Descriptor |
|---|---|---|---|---|---|---|
| 1-40 | B1 | --H | --O-- | --CH₂CH₂-- | 4-oxopiperidin-1-yl | |
| 1-41 | B1 | --H | --O-- | --CH₂CH₂-- | 4-carbamoylpiperidin-1-yl | |
| 1-42 | B1 | --H | --O-- | --CH₂CH₂-- | 4-(methoxycarbonyl)piperidin-1-yl | |
| 1-43 | B1 | --H | --O-- | --CH₂CH₂-- | 1,4-dioxa-8-azaspiro[4.5]decan-8-yl | |
| 1-44 | B1 | --H | --O-- | --CH₂CH₂-- | morpholin-4-yl | |
| 1-45 | B1 | --H | --O-- | --CH₂CH₂-- | 4-phenylpiperazin-1-yl | |
| 1-46 | B1 | --H | --O-- | --(CH₂)₃-- | pyrrolidin-1-yl | |
| 1-47 | B1 | --H | --O-- | --(CH₂)₄-- | pyrrolidin-1-yl | |
| 1-48 | B1 | --CH₃ | --O-- | --CH₂CH₂-- | pyrrolidin-1-yl | |
| 1-49 | B1 | --CH₂CH=CH₂ | --O-- | --CH₂CH₂-- | pyrrolidin-1-yl | |
| 1-50 | B1 | --CH₂OH | --O-- | --CH₂CH₂-- | pyrrolidin-1-yl | |

TABLE 1-continued
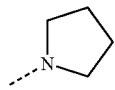
| Co. Nr. | Ex. Nr. | --R² | --Z-- | --Alk^Z-- | --L | Salt/Descriptor |
|---|---|---|---|---|---|---|
| 1-51 | B1 | --CH₂OH | --O-- | --CH₂CH₂-- | 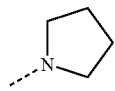 | .0.33 HCl .0.66 HCO₂H |
| 1-52 | B1 | --CH₂OCH₃ | --O-- | --CH₂CH₂-- | 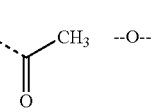 | |
| 1-53 | B1 | 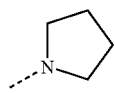 | --O-- | --CH₂CH₂-- | 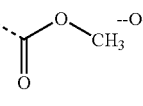 | |
| 1-54 | B1 | 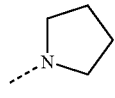 | --O-- | --CH₂CH₂-- | 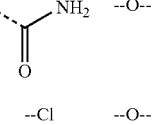 | |
| 1-55 | B1 | 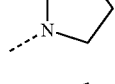 | --O-- | --CH₂CH₂-- | 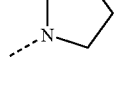 | |
| 1-56 | B1 | --Cl | --O-- | --CH₂CH₂-- |  | |
| 1-57 | B1 | --OCH₃ | --O-- | (cb) | 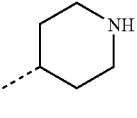 | |
| 1-58 | B1 | --OCH₃ | --O-- | (cb) | 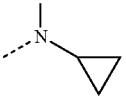 | |
| 1-59 | B1 | --OCH₃ | --O-- | --CH₂—CH₂-- | 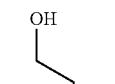 | |
| 1-60 | B1 | --OCH₃ | --O-- | --CH₂CH₂-- | 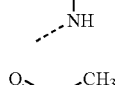 | |
| 1-61 | B1 | --OCH₃ | --O-- | --CH₂CH₂-- | 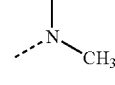 | |
| 1-62 | B1 | --OCH₃ | --O-- | --CH₂CH₂-- |  | |

TABLE 1-continued

| Co. Nr. | Ex. Nr. | --R² | --Z-- | --Alk^Z-- | --L | Salt/Descriptor |
|---|---|---|---|---|---|---|
| 1-63 | B1 | --OCH₃ | --O-- | --CH₂CH₂-- | N,N,N'-trimethyl-glycinamide | |
| 1-64 | B1 | --OCH₃ | --O-- | --CH₂CH₂-- | N-methyl-2-methoxyacetamide | |
| 1-65 | B1 | --OCH₃ | --O-- | --CH₂CH₂-- | N-methyl-cyclopentanecarboxamide | |
| 1-66 | B1 | --OCH₃ | --O-- | --CH₂CH₂-- | N-methyl-benzamide | |
| 1-67 | B1* | --OCH₃ | --O-- | --CH₂CH₂-- | pyrrolidine | •HCl |
| 1-68 | B1 | --OCH₃ | --O-- | --CH₂CH₂-- | 3-hydroxypyrrolidine | RS |
| 1-69 | B1 | --OCH₃ | --O-- | --CH₂CH₂-- | 4-fluoropiperidine | |
| 1-70 | B1 | --OCH₃ | --O-- | --CH₂CH₂-- | 4-fluoropiperidine | •HCl |
| 1-71 | B1 | --OCH₃ | --O-- | --CH₂CH₂-- | 1-methyl-4-cyanopiperidine | |

TABLE 1-continued
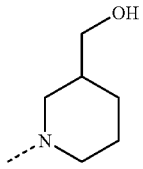
| Co. Nr. | Ex. Nr. | --R² | --Z-- | --Alk^Z-- | --L | Salt/Descriptor |
|---|---|---|---|---|---|---|
| 1-72 | B1 | --OCH₃ | --O-- | --CH₂CH₂-- | 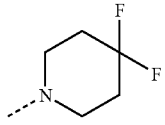 | RS |
| 1-73 | B1 | --OCH₃ | --O-- | --CH₂CH₂-- | 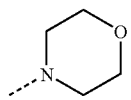 | |
| 1-74 | B1 | --OCH₃ | --O-- | --CH₂CH₂-- | 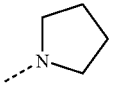 | |
| 1-75 | B1 | --OCH₃ | --O-- | --(CH₂)₃-- | 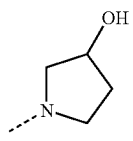 | |
| 1-76 | B1 | --OCH₃ | --O-- | --(CH₂)₃-- | 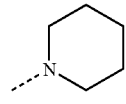 | RS |
| 1-77 | B1 | --OCH₃ | --O-- | --(CH₂)₃-- | 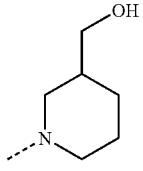 | |
| 1-78 | B1 | --OCH₃ | --O-- | --(CH₂)₃-- | 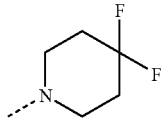 | RS |
| 1-79 | B1 | --OCH₃ | --O-- | --(CH₂)₃-- | 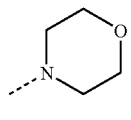 | |
| 1-80 | B1 | --OCH₃ | --O-- | --(CH₂)₃-- | 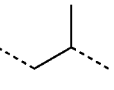 | |
| 1-81 | B1 | --OCH₃ | --O-- | 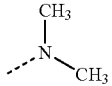 | | |

TABLE 1-continued

| Co. Nr. | Ex. Nr. | --R² | --Z-- | --Alk^Z-- | --L | Salt/ Descriptor |
|---|---|---|---|---|---|---|
| 1-82 | B1 | --OCH₃ | --O-- | (sec-butyl) | pyrrolidin-1-yl | |
| 1-83 | B1 | --OCH₃ | --O-- | (sec-butyl) | --N(CH₃)₂ | |

TABLE 2

| Co. Nr. | Ex. Nr. | (R¹)n-- | --Y²-- | --Alk^Y-- | --Y¹-- | --R² | Salt/ Descriptor |
|---|---|---|---|---|---|---|---|
| 2-01 | B8* | H | (cb) | --(CH₂)₃-- | (cb) | --OCH₃ | |
| 2-02 | B1 | H | (cb) | --CH₂CH₂-- | --NH-- | --H | |
| 2-03 | B1 | H | (cb) | --CH₂CH₂-- | --NH-- | --Cl | |
| 2-04 | B1 | H | (cb) | --CH₂CH₂-- | --NH-- | --OCH₃ | |
| 2-05 | B6 | H | (cb) | --CH₂CH₂-- | --N(CH₃)-- | --OCH₃ | |
| 2-06 | B1 | H | (cb) | --CH₂CH₂-- | --O-- | --OCH₃ | |
| 2-07 | B7* | H | --O-- | --CH₂CH₂-- | (cb) | --OCH₃ | |
| 2-08 | B9* | H | --O-- | --(CH₂)₃-- | (cb) | --OCH₃ | |
| 2-09 | B9 | H | --O-- | --CH₂C≡C-- | (cb) | --OCH₃ | |
| 2-10 | B3 | H | (cb) | --CH₂CH₂-- | --S-- | --H | |
| 2-11 | B3 | H | (cb) | --CH₂CH₂-- | --S-- | --OCH₃ | |
| 2-12 | B6 | H | --O-- | --(CH₂)₃-- | --NH-- | --H | |
| 2-13 | B6 | H | --O-- | --(CH₂)₃-- | --NH-- | --OCH₃ | |
| 2-14 | B3 | H | --O-- | --CH₂CH₂-- | --O-- | --OCH₃ | |
| 2-15 | B1 | 4-F | (cb) | --CH₂CH₂-- | --NH-- | --H | |
| 2-16 | B1 | 4-F | (cb) | --CH₂CH₂-- | --NH-- | --OCH₃ | |
| 2-17 | B1 | 4-F | --O-- | --CH₂CH₂-- | --NH-- | --H | |
| 2-18 | B6 | 4-F | --O-- | --(CH₂)₃-- | --NH-- | --OCH₃ | |
| 2-19 | B6 | 2-Br | (cb) | --CH₂CH₂-- | --NH-- | --OCH₃ | |
| 2-20 | B6 | 3-Br | (cb) | --CH₂CH₂-- | --NH-- | --OCH₃ | |
| 2-21 | B6 | 4-Br | (cb) | --CH₂CH₂-- | --NH-- | --OCH₃ | |
| 2-22 | B6 | 2-Cl | (cb) | --CH₂CH₂-- | --NH-- | --OCH₃ | |
| 2-23 | B6 | 3-Cl | (cb) | --CH₂CH₂-- | --NH-- | --OCH₃ | |
| 2-24 | B6 | 4-Cl | (cb) | --CH₂CH₂-- | --NH-- | --OCH₃ | |
| 2-25 | B3 | 3-Cl | (cb) | --CH₂CH₂-- | --S-- | --OCH₃ | |
| 2-26 | B3 | 4-Cl | (cb) | --CH₂CH₂-- | --S-- | --OCH₃ | |
| 2-27 | B6 | 2-Cl | --O-- | --CH₂CH₂-- | --NH-- | --H | |
| 2-28 | B6 | 2-Cl | --O-- | --CH₂CH₂-- | --NH-- | --OCH₃ | |
| 2-29 | B6 | 2-Cl | --O-- | --(CH₂)₃-- | --NH-- | --OCH₃ | |
| 2-30 | B6 | 3-Cl | --O-- | --CH₂CH₂-- | --NH-- | --OCH₃ | |
| 2-31 | B6 | 3-Cl | --O-- | --(CH₂)₃-- | --NH-- | --OCH₃ | |

TABLE 2-continued

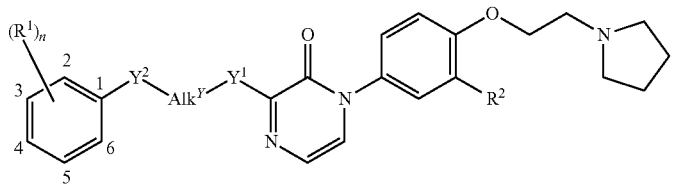

| Co. Nr. | Ex. Nr. | (R¹)n-- | --Y²-- | --Alk^Y-- | --Y¹-- | --R² | Salt/Descriptor |
|---|---|---|---|---|---|---|---|
| 2-32 | B6 | 4-Cl | --O-- | --(CH₂)₃-- | --NH-- | --OCH₃ | |
| 2-33 | B6 | 2-(CH₃) | --O-- | --CH₂CH₂-- | --NH-- | --OCH₃ | |
| 2-34 | B6 | 4-(CF₃) | (cb) | --CH₂CH₂-- | --NH-- | --OCH₃ | |
| 2-35 | B6 | 3-(OCH)₃ | (cb) | --CH₂CH₂-- | --NH-- | --OCH₃ | |
| 2-36 | B6 | 4-(OCH₃) | (cb) | --CH₂CH₂-- | --NH-- | --OCH₃ | |
| 2-37 | B6 | 3-(OCH₃) | --O-- | --(CH₂)₃-- | --NH-- | --OCH₃ | |
| 2-38 | B6 | 4-(OCH₃) | --O-- | --(CH₂)₃-- | --NH-- | --OCH₃ | |
| 2-39 | B6 | 2-Cl, 4-Cl | (cb) | --CH₂CH₂-- | --NH-- | --OCH₃ | |
| 2-40 | B6 | 2-Cl, 4-Cl | --O-- | --CH₂CH₂-- | --NH-- | --OCH₃ | |
| 2-41 | B6 | 2-Cl, 4-Cl | --O-- | --(CH₂)₃-- | --NH-- | --OCH₃ | |
| 2-42 | B6 | 3-Cl, 4-(OCH₃) | (cb) | --CH₂CH₂-- | --NH-- | --OCH₃ | |
| 2-43 | B6 | 2-F, 4-(CF₃) | (cb) | --CH₂CH₂-- | --NH-- | --OCH₃ | |
| 2-44 | B6 | 3-CN | --O-- | --(CH₂)₃-- | --NH-- | --OCH₃ | |

TABLE 3

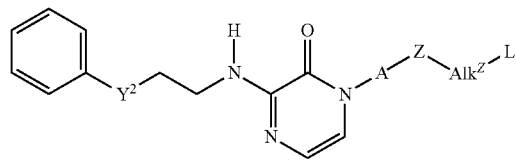

| Co. Nr. | Ex. Nr. | --Y²-- | --A-- | --Z-- | --Alk^Z-- | --L | Salt/Descriptor |
|---|---|---|---|---|---|---|---|
| 3-01 | B5 | (cb) | *p-phenylene* | (cb) | (cb) | ![structure: H₃C-SO₂-N(CH₃)-pyrrolidin-3-yl, N-methyl] | RS |
| 3-02 | B5 | (cb) | *p-phenylene* | (cb) | (cb) | ![structure: HN(CH₃)-pyrrolidin-3-yl, N-methyl] | RS |
| 3-03 | B5 | (cb) | *p-phenylene* | (cb) | (cb) | ![structure: CH₃-C(O)-N(CH₃)-pyrrolidin-3-yl, N-methyl] | RS |

TABLE 3-continued

| Co. Nr. | Ex. Nr. | --Y²-- | --A-- | --Z-- | --Alk^Z-- | --L-- | Salt/Descriptor |
|---|---|---|---|---|---|---|---|
| 3-04 | B5 | (cb) | *para-phenylene* | (cb) | (cb) | N-methyl-N-(1-methylpyrrolidin-3-yl)isobutyramide | RS |
| 3-05 | B5 | (cb) | *para-phenylene* | (cb) | (cb) | tert-butyl methyl(1-methylpyrrolidin-3-yl)carbamate | RS |
| 3-06 | B5 | (cb) | *para-phenylene* | (cb) | (cb) | piperazine | |
| 3-07 | B5 | (cb) | *para-phenylene* | (cb) | (cb) | tert-butyl piperazine-1-carboxylate | |
| 3-08 | B5 | (cb) | 2-methoxy-phenylene | (cb) | (cb) | 1-methylpyrrolidin-3-amine | RS |
| 3-09 | B5 | (cb) | 2-methoxy-phenylene | (cb) | (cb) | N-(1-methylpyrrolidin-3-yl)acetamide | RS |
| 3-10 | B5 | (cb) | 2-methoxy-phenylene | (cb) | (cb) | N-methyl-N-(1-methylpyrrolidin-3-yl)acetamide | RS |

TABLE 3-continued
| Co. Nr. | Ex. Nr. | --Y²-- | --A-- | --Z-- | --Alk^Z-- | --L | Salt/Descriptor |
|---|---|---|---|---|---|---|---|
| 3-11 | B5 | (cb) | 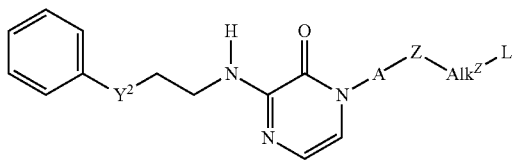 | (cb) | (cb) | 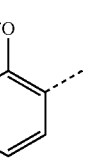 | |
| 3-12 | B5 | (cb) | 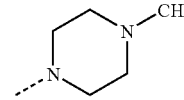 | (cb) | (cb) | 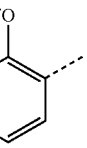 | RS |
| 3-13 | B5 | (cb) | 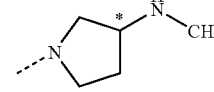 | (cb) | (cb) | 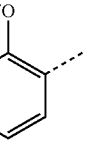 | RS |
| 3-14 | B5 | (cb) | 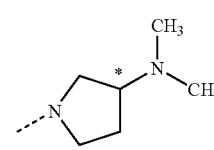 | (cb) | (cb) | 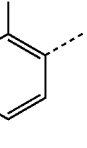 | RS |
| 3-15 | B5 | (cb) | 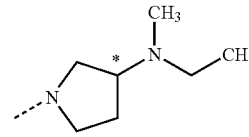 | (cb) | (cb) | 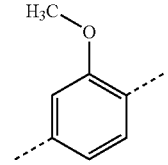 | RS |
| 3-16 | B5 | (cb) | 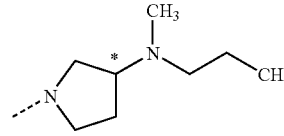 | (cb) | (cb) | 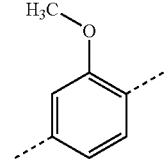 | RS |
| 3-17 | B5 | (cb) | 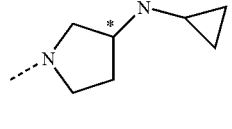 | (cb) | (cb) | 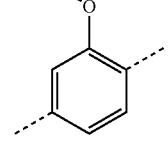 | RS |

TABLE 3-continued

| Co. Nr. | Ex. Nr. | --Y²-- | --A-- | --Z-- | --Alk^Z-- | --L-- | Salt/Descriptor |
|---------|---------|--------|-------|-------|-----------|-------|-----------------|
| 3-18 | B5 | (cb) | 2-methoxyphenyl | (cb) | (cb) | N-(3-(dicyclopropylamino)pyrrolidin-1-yl) | RS |
| 3-19 | B5 | (cb) | 2-methoxyphenyl | (cb) | (cb) | 4-methyl-1,4-diazepan-1-yl | |
| 3-20 | B5 | (cb) | 2-methoxyphenyl | (cb) | (cb) | 3-hydroxy-[1,3'-bipyrrolidin]-1'-yl | RS |
| 3-21 | B5 | (cb) | 2-methoxyphenyl | (cb) | (cb) | 3-morpholinopyrrolidin-1-yl | RS |
| 3-22 | B1 | (cb) | 2-methoxyphenyl | (cb) | but-2-ene | pyrrolidin-1-yl | |
| 3-23 | B1 | (cb) | 2-methoxyphenyl | (cb) | but-2-ene | morpholin-4-yl | |
| 3-24 | B5 | (cb) | 2-methoxyphenyl | --NH-- | (cb) | pyrrolidin-3-yl | RS |

TABLE 3-continued

| Co. Nr. | Ex. Nr. | --Y²-- | --A-- | --Z-- | --Alk^Z-- | --L | Salt/Descriptor |
|---|---|---|---|---|---|---|---|
| 3-25 | B5 | (cb) | 2-methoxyphenyl (H₃C-O-) | --NH-- | (cb) | N-methylpyrrolidin-3-yl | RS |
| 3-26 | B5 | (cb) | 2-methoxyphenyl | --NH-- | (cb) | N-propylpyrrolidin-3-yl | RS |
| 3-27 | B5 | (cb) | 2-methoxyphenyl | --NH-- | (cb) | 3-oxa-9-azabicyclic group | exo *(RS) **(RS) |
| 3-28 | B5 | (cb) | 2-methoxyphenyl | --NH-- | --CH₂CH₂-- | pyrrolidin-1-yl | |
| 3-29 | B5 | (cb) | 2-methoxyphenyl | --NH-- | --CH₂CH₂-- | morpholin-4-yl | |
| 3-30 | B5 | (cb) | 2-methoxyphenyl | --NH-- | --(CH₂)₃-- | morpholin-4-yl | |
| 3-31 | B1 | (cb) | 2-methoxyphenyl | --O-- | (cb) | pyrrolidin-3-yl | RS |

TABLE 3-continued

| Co. Nr. | Ex. Nr. | --Y²-- | --A-- | --Z-- | --Alk^Z-- | --L | Salt/Descriptor |
|---------|---------|--------|-------|-------|-----------|-----|-----------------|
| 3-32 | B1 | (cb) | 2-OMe-phenyl | --O-- | (cb) | 1-methylpyrrolidin-3-yl | RS |
| 3-33 | B1 | (cb) | 2-OMe-phenyl | --O-- | (cb) | 1-cyclopropylpyrrolidin-3-yl | RS |
| 3-34 | B1 | (cb) | 2-OMe-phenyl | --O-- | --CH₂-- | pyrrolidin-2-yl | R |
| 3-35 | B1 | (cb) | 2-OMe-phenyl | --O-- | --CH₂-- | 1-methylpyrrolidin-2-yl | S |
| 3-36 | B1 | (cb) | 2-OMe-phenyl | --O-- | --CH₂-- | 1-Boc-pyrrolidin-2-yl | R |
| 3-37 | B1 | (cb) | 2-OMe-phenyl | --O-- | --CH₂CH₂-- | N-methyl-N-(2-hydroxyethyl)amino | |
| 3-38 | B1 | (cb) | 2-OMe-phenyl | --O-- | --CH₂CH₂-- | NHC(O)CH₃ | |

TABLE 3-continued

| Co. Nr. | Ex. Nr. | --Y²-- | --A-- | --Z-- | --Alk^Z-- | --L-- | Salt/Descriptor |
|---------|---------|--------|-------|-------|-----------|-------|-----------------|
| 3-39 | B1 | (cb) | H₃CO-phenyl | --O-- | --CH₂CH₂-- | -NHC(O)CH₂CH₂CH₃ | |
| 3-40 | B1 | (cb) | H₃CO-phenyl | --O-- | --CH₂CH₂-- | -NHC(O)CH₂N(CH₃)₂ | |
| 3-41 | B1 | (cb) | H₃CO-phenyl | --O-- | --CH₂CH₂-- | -NH-cyclopropyl | |
| 3-42 | B1 | (cb) | H₃CO-phenyl | --O-- | --CH₂CH₂-- | -N(CH₃)-cyclopropyl | |
| 3-43 | B1 | (cb) | H₃CO-phenyl | --O-- | --CH₂CH₂-- | -NHC(O)CH₂OCH₃ | |
| 3-44 | B1 | (cb) | H₃CO-phenyl | --O-- | --CH₂CH₂-- | -NHC(O)-(4-pyridyl) | |
| 3-45 | B1 | (cb) | H₃CO-phenyl | --O-- | --CH₂CH₂-- | 3-hydroxypyrrolidin-1-yl | RS |

TABLE 3-continued

| Co. Nr. | Ex. Nr. | --Y²-- | --A-- | --Z-- | --Alk^Z-- | --L | Salt/Descriptor |
|---------|---------|--------|-------|-------|-----------|-----|-----------------|
| 3-46 | B1 | (cb) | 2-methoxyphenyl | --O-- | --CH₂CH₂-- | 3-fluoropyrrolidin-1-yl (*) | S |
| 3-47 | B1 | (cb) | 2-methoxyphenyl | --O-- | --CH₂CH₂-- | 3-fluoropyrrolidin-1-yl (*) | R |
| 3-48 | B1 | (cb) | 2-methoxyphenyl | --O-- | --CH₂CH₂-- | 2-carbamoylpyrrolidin-1-yl | RS |
| 3-49 | B1 | (cb) | 2-methoxyphenyl | --O-- | --CH₂CH₂-- | 3-(hydroxymethyl)piperidin-1-yl | RS |
| 3-50 | B1 | (cb) | 2-methoxyphenyl | --O-- | --CH₂CH₂-- | 4-fluoropiperidin-1-yl | |
| 3-51 | B1 | (cb) | 2-methoxyphenyl | --O-- | --CH₂CH₂-- | 4-cyanopiperidin-1-yl | |
| 3-52 | B1 | (cb) | 2-methoxyphenyl | --O-- | --CH₂CH₂-- | 3-carbamoylpiperidin-1-yl | RS |

TABLE 3-continued

| Co. Nr. | Ex. Nr. | --Y²-- | --A-- | --Z-- | --Alk^Z-- | --L | Salt/Descriptor |
|---|---|---|---|---|---|---|---|
| 3-53 | B1 | (cb) | H₃C-O-phenyl | --O-- | --CH₂CH₂-- | 1-methylpiperidine-4-carboxamide | |
| 3-54 | B1 | (cb) | H₃C-O-phenyl | --O-- | --CH₂CH₂-- | N-cyclopropyl-1-methylpiperidine-4-carboxamide | |
| 3-55 | B1 | (cb) | H₃C-O-phenyl | --O-- | --CH₂CH₂-- | (1-methylpiperidin-4-yl)(pyrrolidin-1-yl)methanone | |
| 3-56 | B1 | (cb) | H₃C-O-phenyl | --O-- | --CH₂CH₂-- | 4,4-difluoro-1-methylpiperidine | |
| 3-57 | B1 | (cb) | H₃C-O-phenyl | --O-- | --CH₂CH₂-- | 2,6-dimethylpiperidine | * (S) ** (R) |
| 3-58 | B1 | (cb) | H₃C-O-phenyl | --O-- | --CH₂CH₂-- | 1,4-dioxa-8-azaspiro[4.5]decane | |
| 3-59 | B1 | (cb) | H₃C-O-phenyl | --O-- | --CH₂CH₂-- | morpholine | |

TABLE 3-continued

| Co. Nr. | Ex. Nr. | --Y²-- | --A-- | --Z-- | --Alk^Z-- | --L-- | Salt/ Descriptor |
|---|---|---|---|---|---|---|---|
| 3-60 | B1 | (cb) | 4-methoxyphenyl (2,4-disubst, OMe at 2) | --O-- | --CH₂CH₂-- | (S)-3-methylmorpholin-4-yl | S |
| 3-61 | B1 | (cb) | 4-methoxyphenyl (2,4-disubst, OMe at 2) | --O-- | --CH₂CH₂-- | (R)-3-methylmorpholin-4-yl | R |
| 3-62 | B1 | (cb) | 4-methoxyphenyl (2,4-disubst, OMe at 2) | --O-- | --CH₂CH₂-- | 3,5-dimethylmorpholin-4-yl | RS |
| 3-63 | B1 | (cb) | 4-methoxyphenyl (2,4-disubst, OMe at 2) | --O-- | --CH₂CH₂-- | 2,6-dimethylmorpholin-4-yl | * (RS) ** (RS) |
| 3-64 | B1 | (cb) | 4-methoxyphenyl (2,4-disubst, OMe at 2) | --O-- | --CH₂CH₂-- | 2-(hydroxymethyl)morpholin-4-yl | RS |
| 3-65 | B1 | (cb) | 4-methoxyphenyl (2,4-disubst, OMe at 2) | --O-- | --CH₂CH₂-- | 3-oxopiperazin-1-yl |  |
| 3-66 | B1 | (cb) | 4-methoxyphenyl (2,4-disubst, OMe at 2) | --O-- | --(CH₂)₃-- | --NH-C(=O)-CH₃ |  |

TABLE 3-continued

| Co. Nr. | Ex. Nr. | --Y²-- | --A-- | --Z-- | --Alk^Z-- | --L | Salt/ Descriptor |
|---|---|---|---|---|---|---|---|
| 3-67 | B1 | (cb) | H₃C-O-phenyl | --O-- | --(CH₂)₃-- | -NH-C(=O)-CH(CH₃)₂ | |
| 3-68 | B1 | (cb) | H₃C-O-phenyl | --O-- | --(CH₂)₃-- | -N(CH₃)-cyclopropyl | |
| 3-69 | B1 | (cb) | H₃C-O-phenyl | --O-- | --(CH₂)₃-- | -NH-C(=O)-cyclopropyl | |
| 3-70 | B1 | (cb) | H₃C-O-phenyl | --O-- | --(CH₂)₃-- | 3-hydroxy-1-pyrrolidinyl | RS |
| 3-71 | B1 | (cb) | H₃C-O-phenyl | --O-- | --(CH₂)₃-- | 3-(hydroxymethyl)-1-piperidinyl | RS |
| 3-72 | B1 | (cb) | H₃C-O-phenyl | --O-- | --(CH₂)₃-- | 4-fluoro-1-piperidinyl | |
| 3-73 | B1 | (cb) | H₃C-O-phenyl | --O-- | --(CH₂)₃-- | 4-cyano-1-piperidinyl | |

TABLE 3-continued
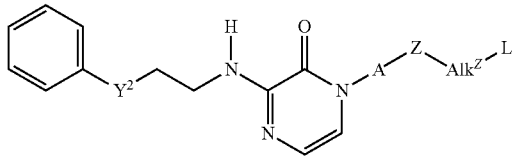
| Co. Nr. | Ex. Nr. | --Y²-- | --A-- | --Z-- | --Alk^Z-- | --L | Salt/Descriptor |
|---|---|---|---|---|---|---|---|
| 3-74 | B1 | (cb) | 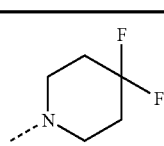 | --O-- | --(CH₂)₃-- | 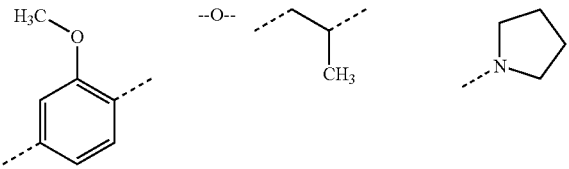 | |
| 3-75 | B1 | (cb) |  | --O-- |  |  | |
| 3-76 | B1 | (cb) |  | --O-- | 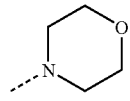 | 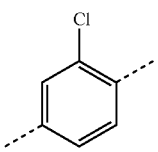 | |
| 3-77 | B1 | (cb) | 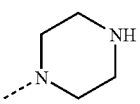 | (cb) | (cb) | 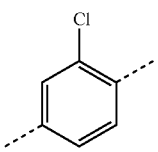 | |
| 3-78 | B1 | (cb) | 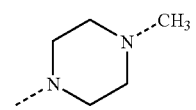 | (cb) | (cb) | 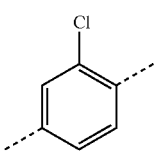 | |
| 3-79 | B1 | (cb) | 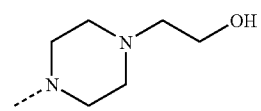 | (cb) | (cb) | 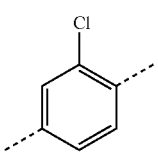 | |
| 3-80 | B1 | (cb) | 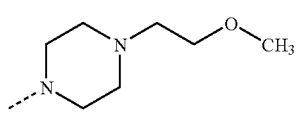 | (cb) | (cb) | 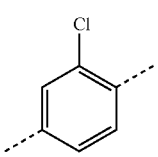 | |
| 3-81 | B1 | (cb) | 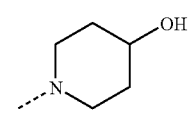 | --O-- | --CH₂CH₂-- | | |

TABLE 3-continued

| Co. Nr. | Ex. Nr. | --Y²-- | --A-- | --Z-- | --Alk^Z-- | --L | Salt/Descriptor |
|---|---|---|---|---|---|---|---|
| 3-82 | B1 | (cb) | 2-Cl-phenyl | --O-- | --CH₂CH₂-- | 4-methylpiperazin-1-yl | |
| 3-83 | B1 | (cb) | 2-Cl-phenyl | --O-- | --CH₂CH₂-- | 4-acetylpiperazin-1-yl | |
| 3-84 | B1 | --O-- | indolin-1,5-diyl | (cb) | --CH₂CH₂-- | N(CH₃)₂ | •HCO₂H |
| 3-85 | B1 | --O-- | indazol-1,5-diyl | (cb) | --CH₂CH₂-- | pyrrolidin-1-yl | |
| 3-86 | B1 | --O-- | quinolin-2,6-diyl | (cb) | --CH₂-- | pyrrolidin-1-yl | |
| 3-87 | B1 | (cb) | quinolin-2,6-diyl | (cb) | (cb) | piperidin-1-yl | |
| 3-88 | B4 | --O-- | pyridin-2,5-diyl | (cb) | (cb) | 1-(N-methyl-N-acetyl)amino-pyrrolidin-3-yl | RS |
| 3-89 | B4 | --O-- | pyridin-2,5-diyl | (cb) | (cb) | 4-hydroxypiperidin-1-yl | |

TABLE 3-continued

| Co. Nr. | Ex. Nr. | --Y²-- | --A-- | --Z-- | --Alk^Z-- | --L | Salt/Descriptor |
|---|---|---|---|---|---|---|---|
| 3-90 | B4 | --O-- | (pyridine) | --NH-- | --CH₂CH₂-- | (pyrrolidine) | |
| 3-91 | B4 | --O-- | (pyridine) | --O-- | --CH₂CH₂-- | (pyrrolidine) | |
| 3-92 | B1 | (cb) | (chromene) | (cb) | --CH₂-- | (morpholine) | |

TABLE 4

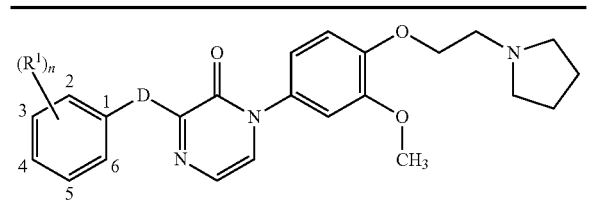

TABLE 4-continued

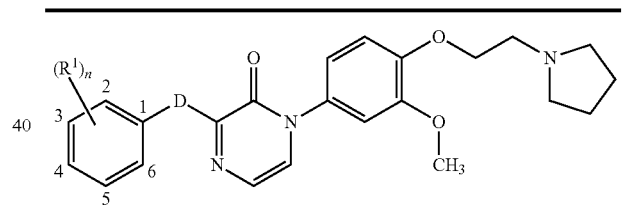

| Co. Nr. | Ex. Nr. | (R¹)n-- | --D-- | Salt/Descriptor | Co. Nr. | Ex. Nr. | (R¹)n-- | --D-- | Salt/Descriptor |
|---|---|---|---|---|---|---|---|---|---|
| 4-01 | B6 | H | (piperidine) | RS | 4-05 | B6 | 3-(CF₃) | (pyrrolidine) | RS |
| 4-02 | B6 | H | (4-oxypiperidine) | | 4-06 | B6 | 2-(OCH₃) | (pyrrolidine) | RS |
| 4-03 | B6 | 4-F | (piperidine) | RS | 4-07 | B6 | 3-(OCH₃) | (pyrrolidine) | RS |
| 4-04 | B6 | 4-(CH₃) | (pyrrolidine) | RS | 4-08 | B6 | 3-Cl, 4-Cl | (pyrrolidine) | RS |

TABLE 5

| Co. Nr. | Ex. Nr. | BD-- | Salt/Descriptor |
|---|---|---|---|
| 5-01 | B6 | tetrahydroisoquinoline-N | |
| 5-02 | B6 | indan-2-yl-NH | |
| 5-03 | B6 | (chroman-2-yl)methyl-NH | RS |
| 5-04 | B6 | (benzo[1,3]dioxol-2-yl)methyl-NH | |
| 5-05 | B6 | biphenyl-4-yl-NH | |
| 5-06 | B6 | 2-(pyridin-2-yl)ethyl-NH | |
| 5-07 | B6 | 2-(pyridin-3-yl)ethyl-NH | |
| 5-08 | B6 | 2-(pyridin-2-yloxy)ethyl-NH | |
| 5-09 | B6 | 3-(pyridin-2-yloxy)propyl-NH | |
| 5-10 | B6 | naphthalen-2-yl-S | |
| 5-11 | B3 | 2-(pyridin-2-yl)ethyl-S | |

TABLE 6

| Co. Nr. | Ex. Nr. | --Z-- | --Alk$^Z$-- | --X | Salt/Descriptor |
|---|---|---|---|---|---|
| 6-01 | B5 | (cb) | (cb) | 3-hydroxypyrrolidin-1-yl | RS |
| 6-02 | B5 | (cb) | (cb) | 3-(methylamino)pyrrolidin-1-yl | S |
| 6-03 | B5 | (cb) | (cb) | 3-(methylamino)pyrrolidin-1-yl | R |
| 6-04 | B5 | (cb) | (cb) | 3-(methylamino)pyrrolidin-1-yl | RS |

TABLE 6-continued
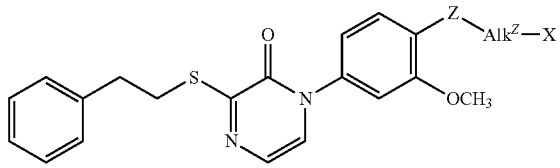
| Co. Nr. | Ex. Nr. | --Z-- | --Alk^Z-- | --X | Salt/Descriptor |
|---|---|---|---|---|---|
| 6-05 | B5 | (cb) | (cb) | 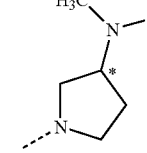 | S |
| 6-06 | B5 | (cb) | (cb) | 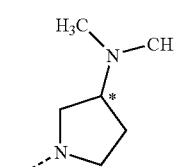 | R |
| 6-07 | B5 | (cb) | (cb) | 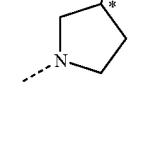 | RS |
| 6-08 | B5 | (cb) | (cb) | 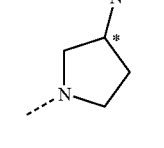 | RS |
| 6-09 | B5 | (cb) | (cb) | 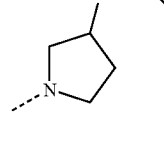 | * (RS) ** (RS) |
| 6-10 | B5 | (cb) | (cb) | 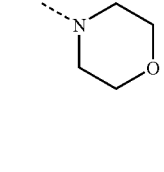 | |
| 6-11 | B5 | (cb) | (cb) |  | |
| 6-12 | B3 | (cb) | 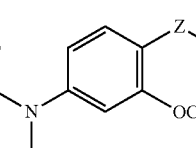 | 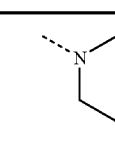 | |
| 6-13 | B3 | (cb) | 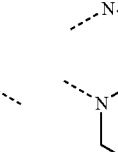 | 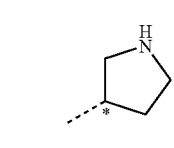 | |
| 6-14 | B3 | --O-- | (cb) | 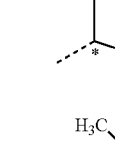 | RS |
| 6-15 | B3 | --O-- | (cb) | 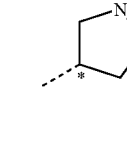 | RS |
| 6-16 | B3 | --O-- | (cb) | 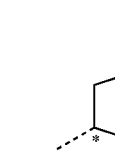 | RS |
| 6-17 | B3 | --O-- | (cb) | 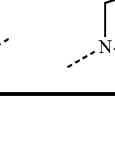 | RS |
| 6-18 | B3 | --NH-- |  | | |

TABLE 7

[Structure: phenoxy-propyl-amino pyrazinone with methoxy-phenyl bearing Z-Alk^Z-X substituent]

| Co. Nr. | Ex. Nr. | --Alk^Z-- | --X | Salt/Descriptor |
|---|---|---|---|---|
| 7-01 | B1 | (cb) | 4-piperidinyl (NH) | trifluoroacetate salt •C$_2$HF$_3$O$_2$ |
| 7-02 | B1 | (cb) | 1-Boc-4-piperidinyl | |
| 7-03 | B1 | --CH$_2$CH$_2$-- | N(CH$_3$)C(O)CH$_3$ | |

TABLE 8

[Structure: B-Y²-ethyl-amino pyrazinone with R²-substituted phenyl bearing Z-Alk^Z-X substituent]

| Co. Nr. | Ex. Nr. | B-- | --Y²-- | -R²-- | --Z-- | --Alk^Z-- | --X | Salt/Descriptor |
|---|---|---|---|---|---|---|---|---|
| 8-01 | B1 | 4-F-phenyl | (cb) | --Cl | --O-- | (cb) | 3-pyrrolidinyl (NH) | RS |
| 8-02 | B1 | 4-F-phenyl | --O-- | --Cl | --O-- | (cb) | 3-pyrrolidinyl* (NH) | RS |
| 8-03 | B1 | 4-F-phenyl | (cb) | --Cl | --O-- | --(CH$_2$)$_2$-- | 3-OH-pyrrolidin-1-yl* | RS |
| 8-04 | B1 | 4-F-phenyl | --O-- | --Cl | --O-- | --(CH$_2$)$_2$-- | 3-OH-pyrrolidin-1-yl* | RS |
| 8-05 | B1 | 4-F-phenyl | (cb) | --Cl | (cb) | (cb) | 4-methylpiperazin-1-yl | |

TABLE 8-continued

| Co. Nr. | Ex. Nr. | B-- | --Y²-- | --R²-- | --Z-- | --Alk^Z-- | --X | Salt/Descriptor |
|---|---|---|---|---|---|---|---|---|
| 8-06 | B1 | 2-chlorophenyl | (cb) | —OCH₃ | --O-- | --(CH₂)₂-- | N(CH₃)C(O)CH₃ | |
| 8-07 | B1 | 2-chlorophenyl | --O-- | —OCH₃ | --O-- | --(CH₂)₂-- | N(CH₃)C(O)CH₃ | |
| 8-08 | B5 | 2-pyridyl | (cb) | —OCH₃ | (cb) | (cb) | 3-(methylamino)pyrrolidin-1-yl | RS |
| 8-09 | B1 | 2-pyridyl | (cb) | --Cl | --O-- | --(CH₂)₂-- | 4-fluoropiperidin-1-yl | |

TABLE 9

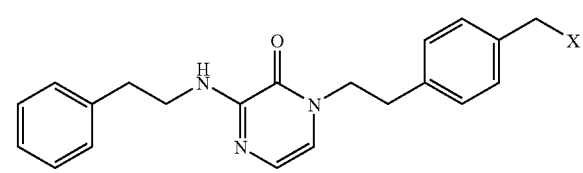

| Co. Nr. | Ex. Nr. | --X | Salt/Descriptor |
|---|---|---|---|
| 9-01 | B10 | pyrrolidin-1-yl | |
| 9-02 | B10 | morpholin-4-yl | |

C. Pharmacological Example

The interaction of the compounds of Formula (I) with MCH-1 receptors was assessed in in vitro transient calcium ($Ca^{2+}$) mobilization assays in the fluorimetric imaging plate reader (FLIPR) format (Sullivan et al. 1999, Methods Mol Biol 114:125-133). In general, the natural agonist (MCH) is incubated with cells expressing the MCH-1 receptor, which elicits a concentration-dependent transient mobilization of $Ca^{2+}$ from internal stores. The interaction of the test compounds with the receptor is assessed in competition experiments. Various concentrations of the test compound are added to the incubation mixture containing the receptor-expressing cells and a submaximal concentration of MCH. The test compound in proportion to its antagonist potency and its concentration inhibits MCH-induced $Ca^{2+}$ mobilization.

Example C.1

Binding Experiment for MCH-1

Cell Culture and Membrane Preparation.

Chinese Hamster ovary cells (CHO) stably expressing the human MCH-1 receptor are grown in a 1:1 mixture of Dulbecco's Modified Eagles Medium (DMEM) and HAM's F12 medium including Glutamax™ (Invitrogen), supplemented with 10% heat-inactivated fetal bovine serum and 400 µg/ml geneticin.

$Ca^{2+}$ Mobilization Experiment for the MCH-1 Receptor

Twenty-four hours before the experiment, MCH-1 receptor-expressing CHO cells are seeded in 20 µl (5,000 cells per well) into 384-well black wall, clear bottom microtiter plates (Costar). On the day of the experiment, 20 µl per well calcium assay kit containing 10 mM probenicide (Molecular Devices) is added. Cells are loaded for 90 min at 37° C. and 5% $CO_2$ in a cell culture incubator. After loading, 20 µl of serial dilutions of the test compound are added and cells are further incubated for 20 min at room temperature in the dark. After 20 min, 20 µl of a submaximal MCH concentration is added and changes in intracellular calcium are recorded directly in a FLIPR III apparatus (Molecular devices).

Data Analysis and Results

Data from assays in the presence of compound were calculated as a percentage of total $Ca^{2+}$-responses measured in the absence of test compound. Inhibition curves, plotting percent of total $Ca^{2+}$-responses versus the log value of the concentration of the test compound, were automatically generated, and sigmoidal inhibition curves were fitted using non-linear regression. The $pIC_{50}$ values of test compounds were derived from individual curves.

All compounds according to Formula (I) produced an inhibition of more than 50% ($pIC_{50}$) at a test concentration ranging between $10^{-6}$ M and $10^{-9}$ M in a concentration-dependent manner.

For a selected number of compounds, covering most of the various embodiments of Formula (I), the results of the in vitro studies are given in Table 10.

TABLE 10

Pharmacological data for compounds according to the invention.

| Compound Nr. | MCH-1 $pIC_{50}$ |
|---|---|
| 1-69 | 8.3 |
| 6-02 | 8.0 |
| 6-05 | 7.9 |
| 6-03 | 7.9 |
| 1-70 | 7.9 |
| 6-17 | 7.8 |
| 6-15 | 7.8 |
| 6-06 | 7.8 |
| 2-13 | 7.8 |
| 9-01 | 7.7 |
| 6-13 | 7.7 |
| 6-07 | 7.7 |
| 3-54 | 7.7 |
| 3-50 | 7.7 |
| 2-11 | 7.7 |
| 1-09 | 7.7 |
| 2-16 | 7.6 |
| 6-16 | 7.6 |
| 6-12 | 7.6 |
| 6-04 | 7.6 |
| 3-81 | 7.6 |
| 3-72 | 7.6 |
| 3-55 | 7.6 |
| 3-41 | 7.6 |
| 3-35 | 7.6 |
| 3-34 | 7.6 |
| 2-31 | 7.6 |
| 2-24 | 7.6 |
| 2-03 | 7.5 |
| 2-10 | 7.5 |
| 8-05 | 7.5 |
| 8-03 | 7.5 |
| 7-03 | 7.5 |
| 7-01 | 7.5 |
| 6-09 | 7.5 |
| 6-08 | 7.5 |
| 3-74 | 7.5 |
| 3-57 | 7.5 |
| 3-49 | 7.5 |
| 3-45 | 7.5 |
| 3-42 | 7.5 |
| 3-22 | 7.5 |
| 2-35 | 7.5 |
| 2-20 | 7.5 |
| 1-49 | 7.5 |
| 1-17 | 7.5 |
| 9-02 | 7.4 |
| 6-01 | 7.4 |
| 3-86 | 7.4 |
| 3-75 | 7.4 |
| 3-73 | 7.4 |
| 3-71 | 7.4 |
| 3-68 | 7.4 |
| 3-62 | 7.4 |

TABLE 10-continued

Pharmacological data for compounds according to the invention.

| Compound Nr. | MCH-1 $pIC_{50}$ |
|---|---|
| 3-56 | 7.4 |
| 3-52 | 7.4 |
| 3-51 | 7.4 |
| 3-31 | 7.4 |
| 3-26 | 7.4 |
| 3-23 | 7.4 |
| 3-11 | 7.4 |
| 3-08 | 7.4 |
| 2-21 | 7.4 |
| 2-18 | 7.4 |
| 2-04 | 7.4 |
| 1-79 | 7.4 |
| 1-18 | 7.4 |
| 1-03 | 7.4 |
| 2-23 | 7.3 |
| 2-36 | 7.3 |
| 1-48 | 7.3 |
| 8-01 | 7.3 |
| 3-83 | 7.3 |
| 3-82 | 7.3 |
| 3-78 | 7.3 |
| 3-76 | 7.3 |
| 3-70 | 7.3 |
| 3-59 | 7.3 |
| 3-58 | 7.3 |
| 3-53 | 7.3 |
| 3-46 | 7.3 |
| 3-37 | 7.3 |
| 3-33 | 7.3 |
| 3-16 | 7.3 |
| 3-15 | 7.3 |
| 3-14 | 7.3 |
| 3-13 | 7.3 |
| 3-02 | 7.3 |
| 2-30 | 7.3 |
| 1-77 | 7.3 |
| 1-73 | 7.3 |
| 1-72 | 7.3 |
| 1-62 | 7.3 |
| 1-67 | 7.2 |
| 6-10 | 7.2 |
| 5-09 | 7.2 |
| 3-79 | 7.2 |
| 3-60 | 7.2 |
| 3-47 | 7.2 |
| 3-39 | 7.2 |
| 3-38 | 7.2 |
| 3-30 | 7.2 |
| 3-29 | 7.2 |
| 3-25 | 7.2 |
| 3-12 | 7.2 |
| 3-09 | 7.2 |
| 3-03 | 7.2 |
| 2-32 | 7.2 |
| 2-29 | 7.2 |
| 2-26 | 7.2 |
| 2-15 | 7.2 |
| 1-83 | 7.2 |
| 1-82 | 7.2 |
| 1-81 | 7.2 |
| 1-80 | 7.2 |
| 1-59 | 7.2 |
| 1-58 | 7.2 |
| 1-57 | 7.2 |
| 3-84 | 7.1 |
| 3-10 | 7.1 |
| 8-09 | 7.1 |
| 5-11 | 7.1 |
| 3-92 | 7.1 |
| 3-80 | 7.1 |
| 3-61 | 7.1 |
| 3-48 | 7.1 |
| 3-40 | 7.1 |
| 3-32 | 7.1 |
| 3-27 | 7.1 |

TABLE 10-continued

Pharmacological data for compounds according to the invention.

| Compound Nr. | MCH-1 pIC$_{50}$ |
|---|---|
| 3-21 | 7.1 |
| 3-17 | 7.1 |
| 2-44 | 7.1 |
| 2-28 | 7.1 |
| 2-07 | 7.1 |
| 2-06 | 7.1 |
| 1-78 | 7.1 |
| 1-74 | 7.1 |
| 1-13 | 7.1 |
| 1-12 | 7.1 |
| 2-22 | 7.0 |
| 1-16 | 7.0 |
| 1-19 | 7.0 |
| 6-14 | 7.0 |
| 5-04 | 7.0 |
| 3-77 | 7.0 |
| 3-64 | 7.0 |
| 3-06 | 7.0 |
| 3-04 | 7.0 |
| 3-01 | 7.0 |
| 2-34 | 7.0 |
| 2-14 | 7.0 |
| 2-12 | 7.0 |
| 1-75 | 7.0 |
| 1-71 | 7.0 |
| 1-65 | 7.0 |
| 1-64 | 7.0 |
| 1-61 | 7.0 |
| 1-53 | 7.0 |
| 1-37 | 7.0 |
| 1-15 | 7.0 |
| 1-11 | 7.0 |
| 1-10 | 7.0 |
| 3-28 | 6.9 |
| 7-02 | 6.9 |
| 6-11 | 6.9 |
| 3-69 | 6.9 |
| 3-67 | 6.9 |
| 3-66 | 6.9 |
| 3-36 | 6.9 |
| 3-20 | 6.9 |
| 3-19 | 6.9 |
| 2-25 | 6.9 |
| 2-02 | 6.9 |
| 2-01 | 6.9 |
| 1-76 | 6.9 |
| 1-68 | 6.9 |
| 1-51 | 6.9 |
| 1-52 | 6.8 |
| 1-24 | 6.8 |
| 8-02 | 6.8 |
| 5-07 | 6.8 |
| 5-06 | 6.8 |
| 3-65 | 6.8 |
| 3-63 | 6.8 |
| 3-18 | 6.8 |
| 3-05 | 6.8 |
| 2-08 | 6.8 |
| 1-42 | 6.8 |
| 1-20 | 6.7 |
| 8-06 | 6.7 |
| 3-87 | 6.7 |
| 3-44 | 6.7 |
| 3-43 | 6.7 |
| 3-24 | 6.7 |
| 2-40 | 6.7 |
| 2-39 | 6.7 |
| 2-33 | 6.7 |
| 1-63 | 6.7 |
| 1-60 | 6.7 |
| 1-54 | 6.7 |
| 1-43 | 6.7 |
| 1-39 | 6.7 |
| 1-02 | 6.6 |
| 5-08 | 6.6 |
| 5-05 | 6.6 |
| 2-42 | 6.6 |
| 2-27 | 6.6 |
| 1-66 | 6.6 |
| 1-40 | 6.6 |
| 1-26 | 6.6 |
| 3-90 | 6.5 |
| 8-08 | 6.5 |
| 8-07 | 6.5 |
| 8-04 | 6.5 |
| 6-18 | 6.5 |
| 5-10 | 6.5 |
| 5-02 | 6.5 |
| 4-04 | 6.5 |
| 2-19 | 6.5 |
| 1-36 | 6.5 |
| 1-31 | 6.5 |
| 1-14 | 6.5 |
| 1-08 | 6.4 |
| 3-85 | 6.4 |
| 5-03 | 6.4 |
| 3-89 | 6.4 |
| 2-37 | 6.4 |
| 1-01 | 6.3 |
| 1-44 | 6.3 |
| 1-21 | 6.3 |
| 3-07 | 6.3 |
| 2-05 | 6.3 |
| 1-35 | 6.3 |
| 1-30 | 6.3 |
| 1-28 | 6.3 |
| 4-07 | 6.2 |
| 4-02 | 6.2 |
| 2-41 | 6.2 |
| 1-41 | 6.2 |
| 1-25 | 6.2 |
| 4-08 | 6.1 |
| 3-88 | 6.1 |
| 2-43 | 6.1 |
| 1-45 | 6.1 |
| 1-33 | 6.1 |
| 1-32 | 6.1 |
| 1-55 | 6.0 |
| 1-47 | 6.0 |
| 1-34 | 6.0 |
| 4-01 | 5.9 |
| 1-23 | 5.9 |
| 1-04 | 5.8 |
| 1-07 | 5.8 |
| 1-38 | 5.8 |
| 1-29 | 5.8 |
| 1-22 | 5.7 |
| 2-17 | 5.7 |
| 4-05 | 5.7 |
| 4-03 | 5.7 |
| 2-38 | 5.7 |
| 1-06 | 5.7 |
| 1-46 | 5.5 |
| 3-91 | 5.4 |
| 4-06 | 5.2 |
| 1-56 | 5.1 |
| 5-01 | 5.1 |
| 1-27 | <5 |
| 1-05 | <5 |

D. Composition Examples

"Active ingredient" (a.i.) as used throughout these examples relates to a final compound of formula (I), the pharmaceutically acceptable acid or base addition salts thereof, the stereochemically isomeric forms thereof, the N-oxide form thereof, a quaternary ammonium salt thereof and prodrugs thereof.

Example D.1

Oral Drops

500 Grams of the a.i. is dissolved in 0.5 l of 2-hydroxypropanoic acid and 1.5 l of the polyethylene glycol at 60-80° c. After cooling to 30-40° C. there are added 35 l of polyethylene glycol and the mixture is stirred well. Then there is added a solution of 1750 grams of sodium saccharin in 2.5 l of purified water and while stirring there are added 2.5 l of cocoa flavor and polyethylene glycol q.s. to a volume of 50 l, providing an oral drop solution comprising 10 mg/ml of a.i. The resulting solution is filled into suitable containers.

Example D.2

Oral Solution

9 Grams of methyl 4-hydroxybenzoate and 1 gram of propyl 4-hydroxybenzoate are dissolved in 4 l of boiling purified water. In 3 l of this solution are dissolved first 10 grams of 2,3-dihydroxybutanedioic acid and thereafter 20 grams of the a.i. The latter solution is combined with the remaining part of the former solution and 12 l, 1,2,3-propanetriol and 3 l of sorbitol 70% solution are added thereto. 40 Grams of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the active ingredient per teaspoonful (5 ml). The resulting solution is filled in suitable containers.

Example D.3

Film-Coated Tablets

Preparation of Tablet Core

A mixture of 100 grams of the a.i., 570 grams lactose and 200 grams starch is mixed well and thereafter humidified with a solution of 5 grams sodium dodecyl sulfate and 10 grams polyvinylpyrrolidone in about 200 ml of water. The wet powder mixture is sieved, dried and sieved again. Subsequently, there is added 100 grams microcrystalline cellulose and 15 grams hydrogenated vegetable oil. The whole is mixed well and compressed into tablets, giving 10,000 tablets, each containing 10 mg of the active ingredient.

Coating

To a solution of 10 grams methyl cellulose in 75 ml of denaturated ethanol there is added a solution of 5 grams of ethyl cellulose in 150 ml of dichloromethane. Subsequently, there are added 75 ml of dichloromethane and 2.5 ml 1,2,3-propanetriol. 10 grams of polyethylene glycol is molten and dissolved in 75 ml of dichloromethane. The latter solution is added to the former and subsequently, there are added 2.5 grams of magnesium octadecanoate, 5 grams of polyvinylpyrrolidone and 30 ml of concentrated color suspension and the whole is homogenated. The tablet cores are coated with the thus obtained mixture in a coating apparatus.

Example D.4

Injectable Solution 1.8 grams methyl 4-hydroxybenzoate and 0.2 grams propyl 4-hydroxybenzoate are dissolved in about 0.5 l of boiling water for injection. After cooling to about 50° C. there are added while stirring 4 grams lactic acid, 0.05 grams propylene glycol and 4 grams of the a.i. The solution is cooled to room temperature and supplemented with water for injection q.s. ad 1 l, giving a solution comprising 4 mg/ml of a.i. The solution is sterilized by filtration and filled in sterile containers.

E. Physico-Chemical Data

General Part A

The HPLC gradient was supplied by an Agilent 1100 module comprising a pump and diode-array detector (DAD) with Gilson 215 autosampler. Flow from the column was split to a MS detector. Ionisation is either electrospray or APCI, depending on type of compound. Typical electrospray conditions use a capillary needle voltage of 3.5 kV and a cone voltage of 25 V. The source temperature was maintained at a temperature between 120-150° C. (the exact temperature was determined on a compound-by-compound basis). Typical APCI conditions use a corona discharge current of 17 µA and a cone voltage of 25 V. The source temperature was maintained at a temperature between 140-160° C. (the exact temperature was determined on a compound-by-compound basis). The desolvation temperature was 350° C. Mass spectra were acquired by scanning from 100 to 1000, for example in 1 second using a dwell time of 0.1 sec. Nitrogen was used as the nebulizer gas.

General Part B

The HPLC gradient was supplied by a Waters 1512 pump with a Waters diode-array detector (DAD) with Gilson 215 autosampler. Flow from the column was split to a MS detector. Ionisation is either electrospray or APCI, depending on type of compound. Typical electrospray conditions use a capillary needle voltage of 3.5 kV and a cone voltage of 25 V. The source temperature was maintained at a temperature between 120-150° C. (the exact temperature was determined on a compound-by-compound basis). Typical APCI conditions use a corona discharge current of 17 µA and a cone voltage of 25 V. The source temperature was maintained at 140-160° C. (the exact temperature was determined on a compound-by-compound basis). The desolvation temperature was 350° C. Mass spectra were acquired by scanning from 100 to 1000, for example in 1 second using a dwell time of 0.1 sec. Nitrogen was used as the nebulizer gas.

General Part C

The HPLC gradient was supplied by a HP 1100 from Agilent Technologies comprising a quaternary pump with degasser, an autosampler, a column oven (set at 40° C.) and diode-array detector (DAD). Flow from the column was split to a MS detector. The MS detector was configured with an electrospray ionization source. Nitrogen was used as the nebulizer gas. The source temperature was maintained at 140° C. Data acquisition was performed with MassLynx-Openlynx software.

E.1 LCMS—Procedure 1

In addition to general procedure A: Reversed phase HPLC was carried out on a Phenomenex Luna 5µ C18 (2) column (4.6×100 mm; plus guard cartridge) with a flow rate of 2 ml/min. Two mobile phases (mobile phase A: water with 0.1% formic acid; mobile phase B: acetonitrile with 0.1% formic acid) were employed to run a gradient condition from 95% A to 95% B with a flow rate of 2 ml/min in 3.5 minutes and hold for 2 minutes. Typically, injection volumes of between 2 μl and 7 μl, inclusive were used.

E.2 LCMS—Procedure 2

In addition to general procedure B: Reversed phase HPLC was carried out on a Waters Xterra MS 5μ C18 column (4.6× 100 mm; plus guard cartridge) with a flow rate of 2 ml/min. Two mobile phases (mobile phase A: water with 7 mM ammonia; mobile phase B: acetonitrile with 7 mM ammonia) were employed to run a gradient condition from 95% A to 95% B with a flow rate of 2 ml/min in 3.5 minutes and hold for 2 minutes. Typically, injection volumes of between 2 μl and 7 μl, inclusive were used.

E.3 LCMS—Procedure 3

In addition to general procedure C: Reversed phase HPLC was carried out on an ACE-C18 column (3.0 μm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucineenkephaline was the standard substance used for the lock mass calibration.

E.4 LCMS—Procedure 4

In addition to general procedure C: Reversed phase HPLC was carried out on an ACE-C18 column (3.0 μm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-enkephaline was the standard substance used for the lock mass calibration.

E.5 LCMS—Procedure 5

In addition to general procedure C: Reversed phase HPLC was carried out on an ACE-C18 column (3.0 μm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-enkephaline was the standard substance used for the lock mass calibration.

E.6 LCMS—Procedure 6

In addition to general procedure C: Same as procedure 3, but using 10 l of injection volume.

E.7 LCMS—Procedure 7

In addition to general procedure C: Reversed phase HPLC was carried out on an XDB-C18 cartridge (3.5 μm, 4.6×30 mm) from Agilent, with a flow rate of 1 ml/min. The gradient conditions used are: 80% A (0.5 g/l ammonium acetate solution), 10% B (acetonitrile), 10% C (methanol) to 50% B and 50% C in 6.0 minutes, to 100% B at 6.5 minutes, kept till 7.0 minutes and equilibrated to initial conditions at 7.6 minutes until 9.0 minutes. Injection volume 5 μl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-enkephaline was the standard substance used for the lock mass calibration.

E.8 LCMS—Procedure 8

In addition to general procedure C: Reversed phase HPLC was carried out on an ACE-C18 column (3.0 μm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. Low-resolution mass spectra (ZQ detector; quadrupole) were acquired by scanning from 100 to 1000 in 1.0 second using a dwell time of 0.3 seconds. The capillary needle voltage was 3 kV. The cone voltage was 20 V and 50 V for positive ionization mode and 20 V for negative ionization mode.

E.9 LCMS—Procedure 9

In addition to general procedure C: Same as procedure 8, but using 10 μl of injection volume.

E.10 LCMS—Procedure 10

In addition to general procedure B: Reversed phase HPLC was carried out on a Waters Xterra MS 5μ C18 column (4.6× 100 mm; plus guard cartridge) with a flow rate of 2 ml/min. Two mobile phases (mobile phase A: water with 7 mM ammonia; mobile phase B: acetonitrile with 7 mM ammonia) were employed to run a gradient condition from 95% A to 95% B with a flow rate of 2 ml/min in 3.5 minutes and hold for 5.5 minutes. Typically, injection volumes of between 2 μl and 7 μl, inclusive were used.

E.11 LCMS—Procedure 11

In addition to general procedure B: Reversed phase HPLC was carried out on a Waters Xterra MS 5μ C18 column (4.6× 100 mm; plus guard cartridge) with a flow rate of 2 ml/min. Two mobile phases (mobile phase A: water with 7 mM ammonia; mobile phase B: acetonitrile with 7 mM ammonia) were employed to run a gradient condition from 95% A to 95% B with a flow rate of 2 ml/min in 3.5 minutes and hold for 4 minutes. Typically, injection volumes of between 2 μl and 7 μl, inclusive were used.

E.12—Melting Points—Procedure 12

For a number of compounds, melting points were determined with a DSC823e (MettlerToledo). Melting points were measured with a temperature gradient of 30° C./minute. Maximum temperature was 400° C.

E.13 Melting Points—Procedure 13

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display.

TABLE 11

Analytical data for the compounds according to the invention.

| Comp. Nr. | $R_t$ | $(MH)^+$ | LCMS-Procedure | Physico-chemical data |
|---|---|---|---|---|
| 1-01 | 2.16 | 406 | 1 | |
| 1-02 | 3.83 | 448 | 2 | |
| 1-03 | 3.44 | 476 | 1 | |
| 1-04 | 4.24 | 506 | 1 | |
| 1-05 | 3.32 | 484 | 1 | |
| 1-06 | 2.1 | 392 | 1 | |
| 1-07 | 3.64 | 434 | 2 | |
| 1-08 | 3.98 | 423 | 3 | |
| 1-09 | 2.15 | 436 | 1 | |
| 1-10 | 4.04 | 450 | 8 | |
| 1-11 | 3.48 | 506 | 1 | |
| 1-12 | 3.41 | 504 | 1 | |
| 1-13 | 3.35 | 436 | 8 | |
| 1-14 | 3.94 | 478 | 8 | |
| 1-15 | 4.44 | 506 | 8 | |
| 1-16 | 4.30 | 417 | 2 | |
| 1-17 | 3.89 | 447 | 8 | (E) |
| 1-18 | 4.56 | 463 | 8 | (E) |
| 1-19 | 2.11 | 394 | 1 | |
| 1-20 | 2.18 | 420 | 2 | |
| 1-21 | 2.15 | 408 | 1 | |
| 1-22 | 2.13 | 408 | 1 | |
| 1-23 | 2.1 | 381 | 1 | |
| 1-24 | 2.33 | 423 | 1 | |
| 1-25 | 2.35 | 463 | 1 | |
| 1-26 | 3.07 | 425 | 2 | m.p.: 103.6° C. (Procedure 12) |
| 1-27 | 1.97 | 452 | 1 | |
| 1-28 | 2.3 | 451 | 1 | |
| 1-29 | 2.25 | 439 | 1 | |
| 1-30 | 3.07 | 423 | 2 | m.p.: 105.9° C. (Procedure 12) |
| 1-31 | 3.42 | 451 | 1 | |
| 1-32 | 2.51 | 485 | 1 | |
| 1-33 | 2.42 | 501 | 1 | |
| 1-34 | 2.25 | 486 | 1 | |
| 1-35 | 3.75 | 421 | 7 | |
| 1-36 | 2.13 | 437 | 1 | |
| 1-37 | 2.90 | 449 | 1 | |
| 1-38 | 3.92 | 435 | 2 | |
| 1-39 | 2.24 | 453 | 1 | |
| 1-40 | 3.20 | 449 | 2 | |
| 1-41 | 2.18 | 478 | 1 | |
| 1-42 | 2.31 | 493 | 1 | |
| 1-43 | 3.38 | 493 | 2 | |
| 1-44 | 2.17 | 437 | 1 | m.p.: 138.1° C. (Procedure 12) |
| 1-45 | 2.53 | 512 | 1 | |
| 1-46 | 2.3 | 435 | 1 | |
| 1-47 | 2.97 | 449 | 1 | |
| 1-48 | 3.77 | 435 | 3 | |
| 1-49 | 2.49 | 461 | 1 | |
| 1-50 | 3.14 | 451 | 9 | |
| 1-51 | 3.14 | 451 | 9 | |
| 1-52 | 3.54 | 465 | 3 | |
| 1-53 | 3.47 | 463 | 3 | |
| 1-54 | 3.47 | 479 | 3 | |
| 1-55 | 2.79 | 464 | 6 | |
| 1-56 | 3.98 | 455 | 3 | |
| 1-57 | 2.86 | 409 | 3 | |
| 1-58 | 3.16 | 437 | 6 | |
| 1-59 | 2.21 | 437 | 1 | |
| 1-60 | 2.13 | 441 | 1 | |
| 1-61 | 3.05 | 453 | 2 | |
| 1-62 | 3.31 | 481 | 1 | |
| 1-63 | 2.24 | 496 | 1 | |
| 1-64 | 2.90 | 483 | 1 | |
| 1-65 | 3.59 | 507 | 1 | |
| 1-66 | 3.43 | 515 | 1 | |
| 1-67 | 3.32 | 451 | 3 | m.p.: 198.7° C. (Procedure 12) |
| 1-68 | 3.10 | 467 | 2 | |
| 1-69 | 2.25 | 483 | 1 | |
| 1-70 | 4.29 | 483 | 3 | m.p.: 234.9° C. (Procedure 13) |
| 1-71 | 2.26 | 490 | 1 | |
| 1-72 | 3.31 | 495 | 2 | |
| 1-73 | 2.42 | 501 | 1 | |
| 1-74 | 3.12 | 467 | 10 | |
| 1-75 | 7.98 | 465 | 10 | |
| 1-76 | 2.28 | 481 | 1 | |
| 1-77 | 2.35 | 479 | 1 | |
| 1-78 | 3.72 | 509 | 2 | |
| 1-79 | 2.44 | 515 | 1 | |
| 1-80 | 3.23 | 481 | 2 | |
| 1-81 | 3.81 | 439 | 2 | |
| 1-82 | 2.36 | 465 | 1 | |
| 1-83 | 2.31 | 439 | 1 | |
| 2-01 | 3.47 | 434 | 3 | |
| 2-02 | 3.27 | 405 | 3 | |
| 2-03 | 4.07 | 439 | 3 | m.p.: 120.2° C. (Procedure 12) |
| 2-04 | 3.51 | 435 | 8 | m.p.: 101.1° C. (Procedure 12) |
| 2-05 | 3.63 | 449 | 3 | |
| 2-06 | 3.44 | 436 | 3 | |
| 2-07 | 3.02 | 436 | 3 | |
| 2-08 | 3.28 | 450 | 3 | |
| 2-09 | 3.06 | 446 | 6 | |
| 2-10 | 4.02 | 422 | 3 | |
| 2-11 | 3.96 | 452 | 3 | m.p.: 79.4° C. (Procedure 12) |
| 2-12 | 3.44 | 435 | 3 | |
| 2-13 | 3.46 | 465 | 3 | |
| 2-14 | 3.22 | 452 | 3 | |
| 2-15 | 3.43 | 423 | 3 | |
| 2-16 | 3.33 | 453 | 3 | |
| 2-17 | 2.29 | 439 | 1 | |
| 2-18 | 3.55 | 483 | 3 | |
| 2-19 | 3.85 | 513 | 3 | |
| 2-20 | 4.14 | 513 | 8 | |
| 2-21 | 4.26 | 513 | 8 | |
| 2-22 | 3.82 | 469 | 3 | |
| 2-23 | 3.83 | 469 | 3 | |
| 2-24 | 3.88 | 469 | 3 | |
| 2-25 | 4.62 | 486 | 3 | |
| 2-26 | 4.68 | 486 | 3 | |
| 2-27 | 2.31 | 455 | 1 | |
| 2-28 | 2.34 | 485 | 1 | |
| 2-29 | 3.83 | 499 | 3 | |
| 2-30 | 2.42 | 485 | 1 | |
| 2-31 | 4.11 | 499 | 6 | |
| 2-32 | 4.04 | 499 | 6 | |
| 2-33 | 2.36 | 465 | 1 | |
| 2-34 | 4.04 | 503 | 3 | |
| 2-35 | 3.22 | 465 | 6 | |
| 2-36 | 3.21 | 465 | 3 | |
| 2-37 | 3.47 | 495 | 3 | |
| 2-38 | 3.34 | 495 | 3 | |
| 2-39 | 4.43 | 503 | 3 | |
| 2-40 | 2.52 | 519 | 1 | |
| 2-41 | 4.47 | 533 | 3 | |
| 2-42 | 3.64 | 499 | 3 | |
| 2-43 | 4.23 | 521 | 3 | |
| 2-44 | 3.29 | 490 | 3 | |
| 3-01 | 3.26 | 468 | 1 | |
| 3-02 | 2.12 | 390 | 1 | |
| 3-03 | 3.28 | 432 | 1 | |
| 3-04 | 3.32 | 460 | 1 | |

TABLE 11-continued

Analytical data for the compounds according to the invention.

| Comp. Nr. | $R_t$ | (MH)$^+$ | LCMS-Procedure | Physico-chemical data |
|---|---|---|---|---|
| 3-05 | 4.20 | 490 | 1 | |
| 3-06 | 2.07 | 376 | 1 | |
| 3-07 | 3.99 | 476 | 1 | |
| 3-09 | 4.13 | 448 | 8 | |
| 3-10 | 4.32 | 462 | 3 | |
| 3-11 | 3.71 | 420 | 3 | |
| 3-12 | 3.42 | 420 | 8 | |
| 3-13 | 4.09 | 434 | 8 | |
| 3-14 | 4.04 | 448 | 3 | |
| 3-15 | 4.64 | 462 | 8 | |
| 3-16 | 4.71 | 446 | 8 | |
| 3-17 | 5.35 | 460 | 8 | |
| 3-18 | 5.90 | 486 | 8 | |
| 3-19 | 3.41 | 434 | 3 | |
| 3-20 | 3.75 | 476 | 3 | |
| 3-21 | 4.52 | 476 | 3 | m.p.: >300° C. (Procedure 13) |
| 3-22 | 3.70 | 431 | 3 | |
| 3-23 | 4.55 | 447 | 3 | |
| 3-24 | 3.15 | 406 | 3 | |
| 3-25 | 3.57 | 420 | 3 | |
| 3-26 | 4.09 | 448 | 8 | |
| 3-27 | 3.78 | 462 | 3 | |
| 3-29 | 4.49 | 450 | 8 | |
| 3-30 | 4.47 | 464 | 3 | m.p.: >300° C. (Procedure 13) |
| 3-31 | 3.07 | 407 | 3 | m.p.: 151.6° C. (Procedure 13) |
| 3-32 | 3.42 | 421 | 3 | |
| 3-33 | 4.66 | 447 | 3 | |
| 3-34 | 2.08 | 421 | 1 | |
| 3-35 | 2.14 | 435 | 1 | |
| 3-36 | 4.10 | 521 | 1 | |
| 3-37 | 3.35 | 439 | 6 | |
| 3-38 | 3.55 | 423 | 3 | |
| 3-39 | 4.08 | 451 | 3 | |
| 3-40 | 3.74 | 466 | 3 | |
| 3-41 | 3.97 | 421 | 3 | |
| 3-42 | 4.62 | 435 | 3 | |
| 3-43 | 3.75 | 453 | 3 | |
| 3-44 | 3.79 | 486 | 3 | |
| 3-45 | 3.09 | 451 | 2 | |
| 3-46 | 2.17 | 453 | 1 | |
| 3-47 | 2.18 | 453 | 1 | |
| 3-48 | 4.20 | 478 | 3 | |
| 3-49 | 3.25 | 479 | 2 | |
| 3-50 | 4.34 | 467 | 3 | |
| 3-51 | 2.92 | 474 | 1 | |
| 3-52 | 3.69 | 492 | 6 | |
| 3-53 | 3.39 | 492 | 6 | |
| 3-54 | 3.79 | 532 | 6 | |
| 3-55 | 4.12 | 546 | 3 | |
| 3-56 | 2.42 | 485 | 1 | |
| 3-57 | 2.40 | 477 | 1 | |
| 3-58 | 4.22 | 507 | 6 | |
| 3-59 | 2.24 | 451 | 1 | |
| 3-60 | 2.18 | 465 | 1 | |
| 3-61 | 2.26 | 465 | 1 | |
| 3-62 | 2.20 | 479 | 1 | |
| 3-63 | 2.33 | 479 | 1 | |
| 3-64 | 2.91 | 481 | 2 | |
| 3-65 | 2.26 | 464 | 1 | |
| 3-66 | 3.74 | 437 | 3 | |
| 3-67 | 4.26 | 465 | 3 | |
| 3-68 | 2.30 | 449 | 1 | |
| 3-69 | 4.13 | 463 | 3 | |
| 3-70 | 2.29 | 465 | 1 | |
| 3-71 | 2.31 | 493 | 1 | |
| 3-72 | 2.36 | 481 | 1 | |
| 3-73 | 2.31 | 488 | 1 | |
| 3-74 | 2.40 | 499 | 1 | |
| 3-75 | 9.32 | 449 | 11 | |
| 3-76 | 2.24 | 465 | 1 | |
| 3-77 | 3.62 | 410 | 3 | |
| 3-78 | 4.69 | 424 | 3 | |
| 3-79 | 4.32 | 454 | 3 | |
| 3-80 | 4.96 | 468 | 3 | |
| 3-81 | 4.08 | 469 | 3 | m.p.: 151.2° C. (Procedure 13) |
| 3-82 | 4.18 | 468 | 3 | |
| 3-83 | 4.37 | 496 | 3 | m.p.: 121.8° C. (Procedure 13) |
| 3-84 | 3.48 | 420 | 6 | |
| 3-85 | 3.58 | 445 | 3 | |
| 3-86 | 3.59 | 442 | 3 | |
| 3-87 | 5.59 | 426 | 8 | |
| 3-88 | 3.57 | 449 | 6 | |
| 3-90 | 2.60 | 421 | 3 | |
| 3-91 | 2.93 | 422 | 4 | |
| 3-92 | 4.80 | 445 | 3 | |
| 4-01 | 4.35 | 475 | 3 | |
| 4-02 | 3.95 | 491 | 3 | |
| 4-03 | 4.33 | 493 | 3 | |
| 4-04 | 4.16 | 475 | 3 | |
| 4-05 | 4.36 | 529 | 3 | |
| 4-06 | 3.86 | 491 | 3 | |
| 4-07 | 3.68 | 491 | 3 | |
| 4-08 | 4.67 | 529 | 3 | |
| 5-01 | 3.68 | 447 | 3 | |
| 5-02 | 3.49 | 447 | 6 | |
| 5-03 | 3.68 | 477 | 5 | |
| 5-04 | 3.21 | 465 | 6 | |
| 5-05 | 4.89 | 483 | 3 | |
| 5-06 | 3.33 | 436 | 2 | |
| 5-07 | 3.32 | 436 | 2 | |
| 5-08 | 2.03 | 452 | 1 | |
| 5-09 | 2.01 | 466 | 1 | |
| 5-10 | 4.29 | 474 | 3 | |
| 5-11 | 1.62 | 453 | 1 | |
| 6-01 | 4.73 | 424 | 3 | |
| 6-02 | 4.19 | 437 | 3 | |
| 6-03 | 4.15 | 437 | 3 | |
| 6-04 | 4.14 | 437 | 3 | m.p.: 113.2° C. (Procedure 13) |
| 6-05 | 4.77 | 451 | 3 | |
| 6-06 | 4.79 | 451 | 3 | |
| 6-07 | 4.75 | 451 | 3 | m.p.: 126.5° C. (Procedure 13) |
| 6-08 | 4.93 | 479 | 3 | m.p.: 105.5° C. (Procedure 13) |
| 6-09 | 5.22 | 519 | 3 | |
| 6-10 | 4.94 | 424 | 8 | |
| 6-11 | 4.62 | 438 | 3 | |
| 6-12 | 4.54 | 448 | 8 | |
| 6-13 | 5.05 | 464 | 3 | |
| 6-14 | 3.88 | 424 | 3 | |
| 6-15 | 4.16 | 438 | 3 | |
| 6-16 | 4.43 | 466 | 8 | |
| 6-17 | 4.74 | 466 | 8 | |
| 6-18 | 5.16 | 465 | 3 | m.p.: >300° C. (Procedure 13) |
| 7-01 | 3.35 | 451 | 3 | |
| 7-02 | 5.46 | 551 | 3 | |
| 7-03 | 2.86 | 467 | 1 | |
| 8-01 | 3.74 | 429 | 3 | |
| 8-02 | 3.54 | 445 | 3 | |
| 8-03 | 4.02 | 473 | 3 | |
| 8-04 | 3.92 | 489 | 3 | |
| 8-05 | 4.75 | 442 | 3 | |
| 8-06 | 3.26 | 471 | 2 | |
| 8-07 | 3.17 | 487 | 2 | |
| 8-08 | 9.22 | 421 | 10 | |
| 8-09 | 3.24 | 472 | 2 | |
| 9-01 | 3.22 | 403 | 3 | m.p.: 177° C. (Procedure 13) |
| 9-02 | 4.30 | 419 | 3 | |

The invention claimed is:
1. Compound according to general Formula (I)

(R¹)ₙ—B—D—[pyrimidinone ring with N-Alk^X-A(Z-Alk^Z-X)(R²) and R⁸]  (I)

wherein
A is phenyl;
B is phenyl;
D is a radical of formula $Y^2$-$Alk^Y$-$Y^1$; provided that the backbone of D is at least 3 atoms long;
Z, $Y^1$, $Y^2$ are each, independently from each other, selected from the group of a covalent bond; —O—; —NR⁷—; —S—; —SO—; and —SO₂; wherein R⁷ is hydrogen or alkyl;
$Alk^X$-, is a covalent bond and $Alk^Y$, and $Alk^Z$ are each, independently from each other, a covalent bond or a saturated or unsaturated $C_{1-6}$ hydrocarbon radical, wherein one or more hydrogen atoms in each moiety $Alk^Y$ and $Alk^Z$ may optionally be replaced by a radical selected from the group of halo, cyano, hydroxy, amino, oxo and formyl;
R¹ represents one or more substituents selected from the group of halo; cyano; hydroxy; amino; nitro; thio; formyl; alkyl; alkyloxy; alkylcarbonyl and mono- or di(alkyl)amino;
n is an integer, equal to 0, 1, or 2;
R² represents one or more substituents selected from the group of halo; cyano; hydroxy; amino; formyl; alkyl; alkyloxy; alkyloxyalkyl; mono- and di(alkyl)amino; mono- and di(alkyl)aminoalkyl; alkylcarbonyl alkyloxycarbonyl; aminocarbonyl; mono- and di(alkyl)aminocarbonyl; Het¹; and Het¹carbonyl;
X is a radical selected from the group of NR³R⁴ and Pir²;
R³, R⁴ each independently from each other, is selected from the group of hydrogen; alkyl; alkylcarbonyl; NRᵃRᵇ and (C=O)NRᵃRᵇ; wherein each of Rᵃ and Rᵇ is independently selected from alkyl, aryl and alkylaryl; aryl; aryloxy; Het²; and alkyl substituted with one or more radicals selected from the group of NRᵃRᵇ and (C=O)NRᵃRᵇ; wherein each of Rᵃ and Rᵇ is independently selected from alkyl, aryl and alkylaryl; aryl; alkyloxy; alkyloxycarbonyl; alkylsulphonyl; aryloxy and Het²;
R⁸ represents one or more substituents selected from the group of hydrogen, halo, cyano, hydroxy, amino, carboxy, alkyl, alkyloxy, alkylcarbonyl, mono or dialkylamino, nitro, thio, aryl, heteroaryl and formyl;
Pir² is a radical selected from the group of azetidinyl, pyrrolyl, pyrazolyl, imidazolyl, pyridinyl, pyrimidinyl, pyrazinyl, pyridazinyl, pyrrolidinyl, imidazolidinyl, pyrazolidinyl, piperidinyl, homopiperidnyl, diazepyl, morpholinyl, thiomorpholinyl, piperazinyl, imidazolidinyl, imidazolinyl, pyrazolinyl, 1,2,3,4-tetrahydro-isoquinolinyl, indolyl and isoindolyl; wherein each Pir-radical is optionally substituted by one or more radicals selected from the group of halo, hydroxy, oxo, amino, aminocarbonyl, alkyl, alkyloxy, alkylcarbonyl, alkyloxycarbonyl, phenyl; and NR⁵R⁶, wherein R⁵ and R⁶ are independently from each other, selected from the group of hydrogen, alkyl, alkylcarbonyl, alkyloxycarbonyl and alkylsulphonyl;
Het¹ is pyrrolidinyl;
Het² is pyridinyl;
aryl is naphthalenyl or phenyl, each optionally substituted with 1, 2 or 3 substituents, each independently from each other, selected from the group of halo, cyano, hydroxy, amino, alkylamino, alkyloxyalkylamino, oxo, carboxy, nitro, thio, formyl and alkyloxy; and
alkyl is a saturated, straight or branched hydrocarbon radical having from 1 to 6 carbon atoms; or is a saturated, cyclic hydrocarbon radical having from 3 to 7 carbon atoms; or is a saturated, cyclic hydrocarbon radical having from 3 to 7 carbon atoms attached to a saturated, straight or branched hydrocarbon radical having from 1 to 6 carbon atoms; each radical may optionally be substituted on one or more carbon atoms with one or more radicals selected from the group of halo, cyano, hydroxy, amino, oxo, carboxy, nitro, thio and formyl.

2. Compound according to claim 1, characterized in that $Y^1$ and $Y^2$ are each, independently from each other, selected from the group of a covalent bond; —O—; —NR⁷—; and —S—; wherein R⁷ is hydrogen or alkyl.

3. Compound according to claim 2, characterized in that $Y^1$ is selected from the group of —NR⁷—; and —S—; wherein R⁷ is hydrogen or alkyl.

4. Compound according to claim 2, characterized in that $Y^2$ is selected from the group of a covalent bond and —O—.

5. Compound according to claim 2 wherein $Alk^Y$ is selected from the group of —CH₂CH₂— and —CH₂CH₂CH₂—, wherein one or more hydrogen atoms in each moiety $Alk^Y$ and $Alk^Z$ may optionally be replaced by an oxo-radical.

6. Compound according to claim 2, characterized in that D is selected from the group of —OCH₂CH₂NH—, —CH₂CH₂NH— and —OCH₂CH₂CH₂NH—.

7. Compound according to claim 1, characterized in that Z is selected from the group of a covalent bond; —O— and —NH—.

8. Compound according to claim 1, characterized in that $Alk^Z$ is selected from the group of a covalent bond, —CH=CHCH₂—, —CH₂CH₂—, —CH₂CH₂CH₂— and —CH₂CH₂CH₂CH₂—.

9. Compound according to claim 1, characterized in that Pir² is selected from the group of pyrrolidinyl; piperidinyl; morpholinyl; and piperazinyl; wherein each Pir-radical is optionally substituted by one or more radicals selected from the group of hydroxy; and NR⁵R⁶, wherein R⁵ and R⁶ are independently from each other, selected from the group of hydrogen, alkyl, alkylcarbonyl, alkyloxycarbonyl and alkylsulphonyl.

10. Compound according to claim 1 wherein
A is phenyl;
B is phenyl;
D is a radical of formula $Y^2$-$Alk^Y$-$Y^1$; provided that the backbone of D is at least 3 atoms long;
Z, $Y^1$, $Y^2$ are each, independently from each other, selected from the group of a covalent bond; —O—; —NR⁷—; and —S—; wherein R⁷ is hydrogen or alkyl;
$Alk^X$, is a covalent bond and $Alk^Y$, and $Alk^Z$ are each, independently from each other, a covalent bond or a saturated or unsaturated $C_{1-6}$hydrocarbon radical; wherein one or more hydrogen atoms in each moiety $Alk^Y$ and $Alk^Z$ may optionally be replaced by an oxo-radical;
R¹ represents one or more substituents selected from the group of halo and alkyloxy;

$R^2$ represents one or more substituents selected from the group of halo; alkyl; alkyloxy; alkyloxyalkyl; alkylcarbonyl; alkyloxycarbonyl; and aminocarbonyl;

$R^3$, $R^4$ each independently from each other, selected from the group of alkyl alkylcarbonyl and alkyl substituted with one or more radicals selected from the group of di(alkyl)amino; aryl and $Het^2$;

$R^8$ is hydrogen;

$Pir^2$ is a radical selected from the group of pyrrolidinyl, piperidinyl, morpholinyl, and piperazinyl; wherein each Pir-radical is optionally substituted by one or more radicals selected from the group of hydroxy and $NR^5R^6$, wherein $R^5$ and $R^6$ are independently from each other, selected from the group of hydrogen, alkyl, alkylcarbonyl, alkyloxycarbonyl and alkylsulphonyl;

$Het^2$ is pyridinyl; and aryl is phenyl.

11. Pharmaceutical composition comprising a pharmaceutically acceptable carrier or diluent and, as active ingredient, a therapeutically effective amount of a compound according to claim 1 or 10.

12. Pharmaceutical composition according to claim 11, characterized in that it is in a form suitable to be orally administered.

13. Process for the preparation of a pharmaceutical composition as claimed in any one of claims 11 to 12, characterized in that a pharmaceutically acceptable carrier is intimately mixed with a therapeutically effective amount of a compound as claimed in any one of claims 1, 2, 4, 5-9 and 10.

* * * * *